United States Patent [19]
Gordon et al.

[11] Patent Number: 5,713,910
[45] Date of Patent: Feb. 3, 1998

[54] NEEDLE GUIDANCE SYSTEM FOR ENDOSCOPIC SUTURE DEVICE

[75] Inventors: Norman S. Gordon, Irvine; Robert P. Cooper, Yorba Linda; Richard L. Quick, Trabuco Canyon, all of Calif.

[73] Assignee: Laurus Medical Corporation, Irvine, Calif.

[21] Appl. No.: 554,743

[22] Filed: Nov. 7, 1995

Related U.S. Application Data

[63] Continuation-in-part of Ser. No. 311,967, Sep. 26, 1994, Pat. No. 5,578,044, which is a continuation-in-part of Ser. No. 205,042, Mar. 2, 1994, Pat. No. 5,540,704, which is a continuation-in-part of Ser. No. 57,699, May 4, 1993, Pat. No. 5,458,609, which is a continuation-in-part of Ser. No. 941,382, Sep. 4, 1992, Pat. No. 5,364,408.

[51] Int. Cl.⁶ .................................................. A61B 17/00
[52] U.S. Cl. .......................... 606/144; 606/139; 606/147; 112/169
[58] Field of Search ...................... 606/139, 144, 606/145, 147, 148, 185, 186, 187, 278; 112/80.03, 169

[56] References Cited

U.S. PATENT DOCUMENTS

| | | |
|---|---|---|
| 342,773 | 6/1886 | Bailey. |
| 919,138 | 4/1909 | Drake et al.. |
| 1,037,864 | 9/1912 | Carlson et al.. |
| 1,449,087 | 3/1923 | Bugbee. |
| 1,815,725 | 7/1931 | Pilling et al.. |
| 1,822,330 | 9/1931 | Ainslie. |
| 2,577,240 | 12/1951 | Findley. |
| 2,579,192 | 12/1951 | Kohl. |
| 3,013,559 | 12/1961 | Thomas. |
| 3,160,157 | 12/1964 | Chisman. |
| 3,470,875 | 10/1969 | Johnson. |
| 3,638,653 | 2/1972 | Berry. |
| 3,840,017 | 10/1974 | Violante. |
| 3,918,455 | 11/1975 | Coplan. |
| 3,946,740 | 3/1976 | Bassett. |
| 4,161,951 | 7/1979 | Scanlan, Jr.. |
| 4,164,225 | 8/1979 | Johnson et al.. |
| 4,224,947 | 9/1980 | Fukuda. |
| 4,235,177 | 11/1980 | Arbuckle. |
| 4,236,470 | 12/1980 | Stenson. |
| 4,312,337 | 1/1982 | Donohue. |
| 4,345,601 | 8/1982 | Fukuda. |
| 4,493,323 | 1/1985 | Albright et al.. |
| 4,557,265 | 12/1985 | Andersson. |
| 4,596,249 | 6/1986 | Freda et al.. |

(List continued on next page.)

FOREIGN PATENT DOCUMENTS

| | | |
|---|---|---|
| 647813 | 9/1962 | Canada. |
| 0 140 557 | 5/1985 | European Pat. Off.. |
| 0 589 409 | 3/1994 | European Pat. Off.. |
| 0 674 875 | 10/1995 | European Pat. Off.. |
| 969254 | 10/1982 | U.S.S.R. ................ 606/148 |

(List continued on next page.)

*Primary Examiner*—Jeffrey A. Schmidt
*Attorney, Agent, or Firm*—Dennis H. Epperson

[57] ABSTRACT

A method and device for the placement of sutures and for the purpose of approximating tissue. A particular utility is effected in the approximation of the tissue separated by means of an endosurgical trocar being inserted into a body cavity. The invention provides for the loading of suture material including needles into the device, introduction and placement of the device into the body cavity, with the distal end having deployable needle guides, extending the needle guides either simultaneously or individually to the periphery of the wound, engaging the wound with the needle guides, driving the needles and suture material through the tissue to be approximated into a catch mechanism, retracting the needle guides and withdrawing the device, leaving a loop of suture material in the margin of tissue. The suture may then be tied to approximate the wound and excess suture material cut off. The invention also provides for the placement of sutures for the endoscopic approximation, fixation, and ligation of tissues within a body cavity including the driving and retrieval of needle and suture combinations, and facilitating the tying of knots.

48 Claims, 12 Drawing Sheets

U.S. PATENT DOCUMENTS

| | | |
|---|---|---|
| 4,602,635 | 7/1986 | Mulhollan et al. . |
| 4,621,640 | 11/1986 | Mulhollan et al. . |
| 4,635,638 | 1/1987 | Weintraub et al. . |
| 4,781,190 | 11/1988 | Lee . |
| 4,890,615 | 1/1990 | Caspari et al. . |
| 4,898,155 | 2/1990 | Ovil et al. . |
| 4,899,746 | 2/1990 | Brunk . |
| 4,923,461 | 5/1990 | Caspari et al. . |
| 4,926,860 | 5/1990 | Stice et al. . |
| 4,935,027 | 6/1990 | Yoon . |
| 4,957,498 | 9/1990 | Caspari et al. . |
| 5,037,433 | 8/1991 | Wilk et al. . |
| 5,047,039 | 9/1991 | Avant et al. . |
| 5,067,957 | 11/1991 | Jervis . |
| 5,100,415 | 3/1992 | Hayhurst . |
| 5,100,418 | 3/1992 | Yoon et al. . |
| 5,100,421 | 3/1992 | Christoudias . |
| 5,188,636 | 2/1993 | Fedotov . |
| 5,306,281 | 4/1994 | Beurrier . |
| 5,308,353 | 5/1994 | Beurrier . |
| 5,324,298 | 6/1994 | Phillips et al. ............................ 606/148 |
| 5,364,408 | 11/1994 | Gordon . |
| 5,387,221 | 2/1995 | Bisgaard . |
| 5,389,103 | 2/1995 | Melzer et al. . |
| 5,391,174 | 2/1995 | Weston . |
| 5,417,699 | 5/1995 | Klein et al. . |
| 5,458,609 | 10/1995 | Gordon . |
| 5,573,542 | 11/1996 | Stevens ................................... 606/148 |

FOREIGN PATENT DOCUMENTS

| | | |
|---|---|---|
| 1028320 | 7/1983 | U.S.S.R. . |
| 1093329 | 5/1984 | U.S.S.R. . |
| 18602 | 9/1909 | United Kingdom . |
| 2 247 841 | 3/1992 | United Kingdom . |
| WO/90/03766 | 4/1990 | WIPO . |
| WO/92/12674 | 8/1992 | WIPO . |
| WO/93/01750 | 2/1993 | WIPO . |
| WO/94/05123 | 3/1994 | WIPO . |
| WO/94/13211 | 6/1994 | WIPO . |

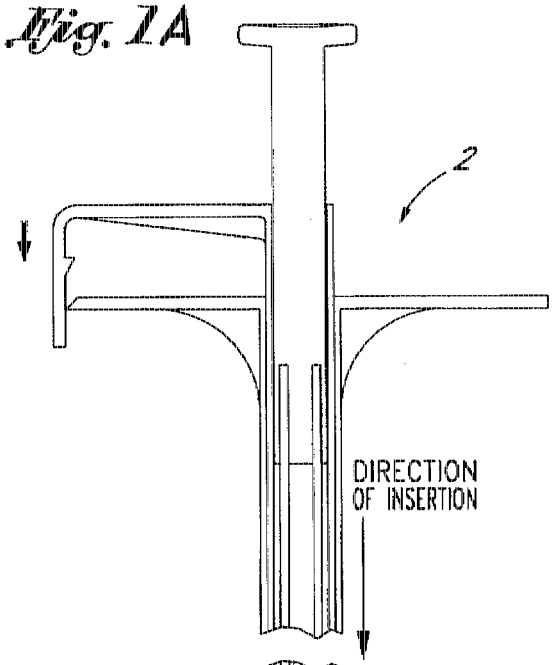
Fig. 1A
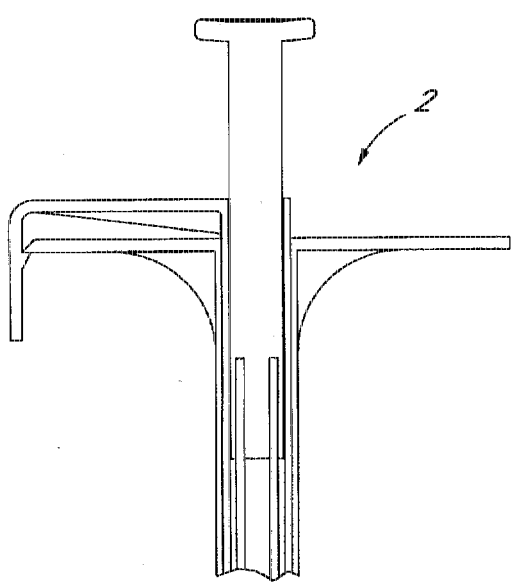
Fig. 1B
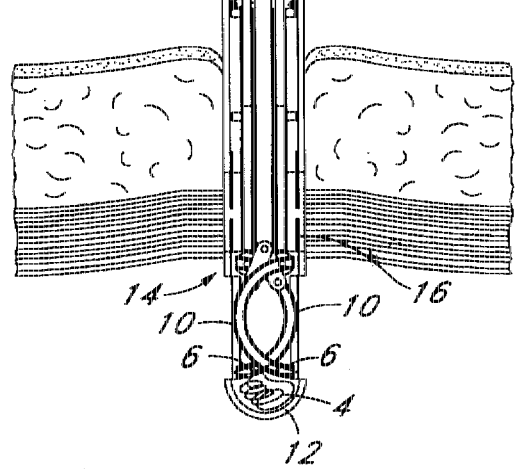
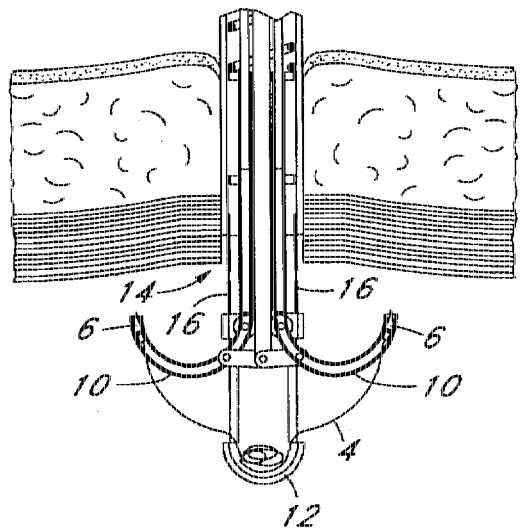

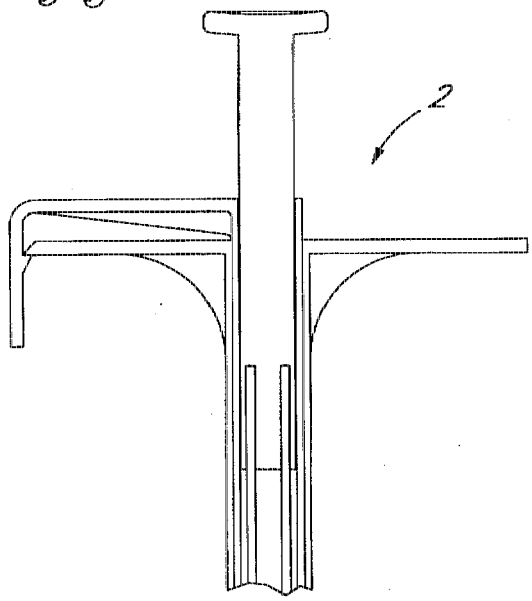
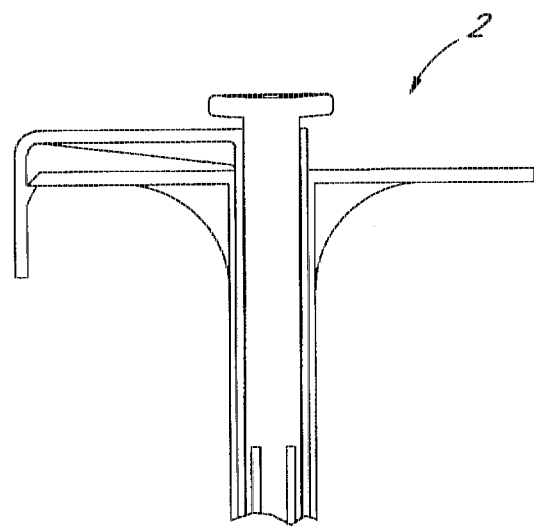
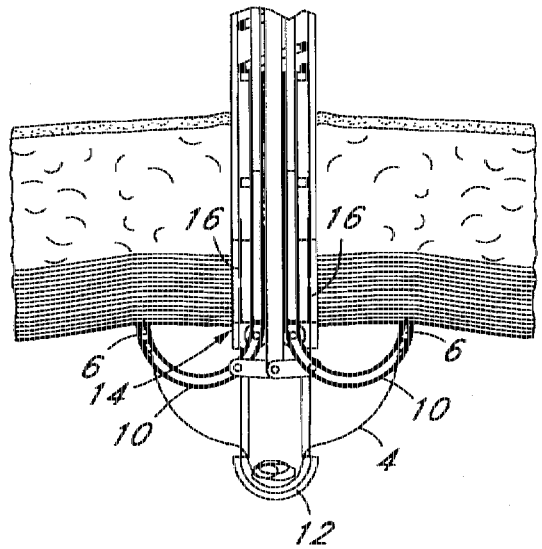
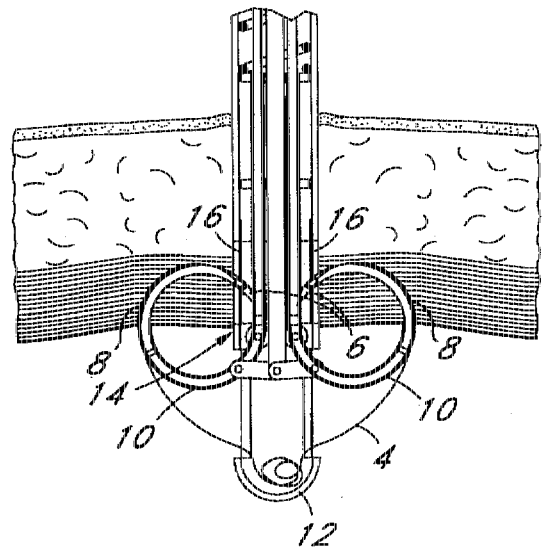

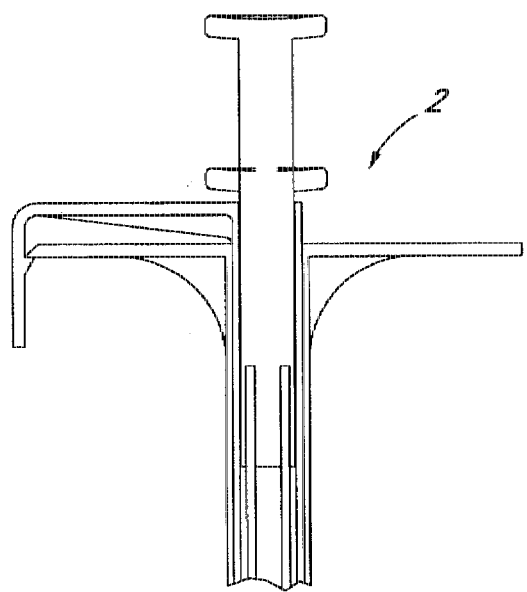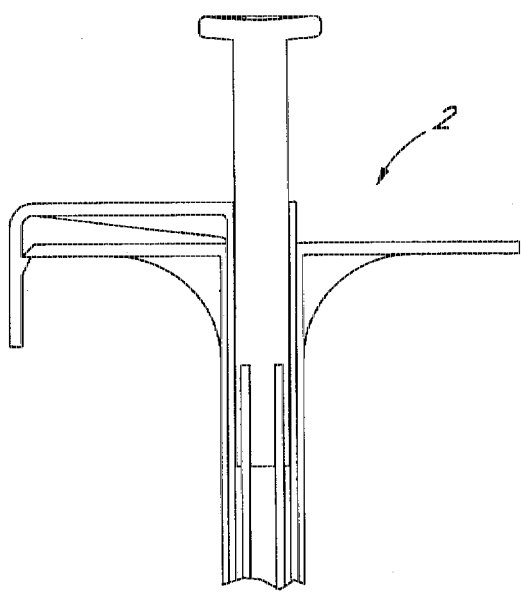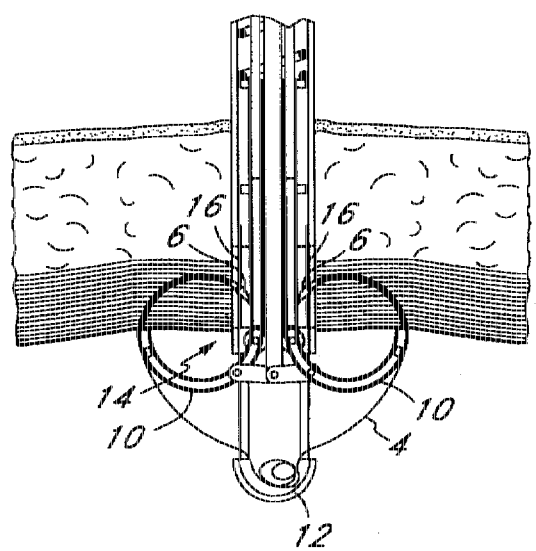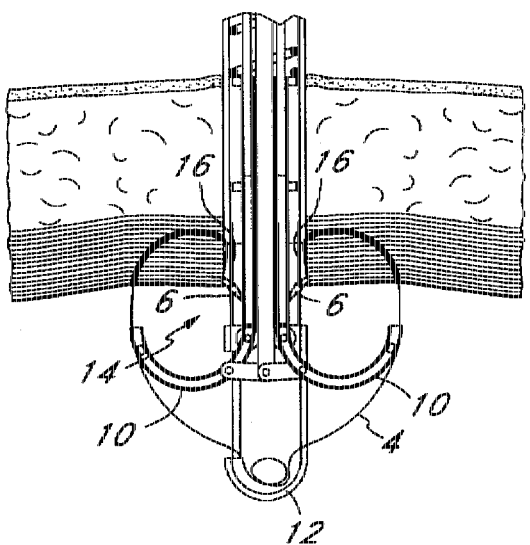

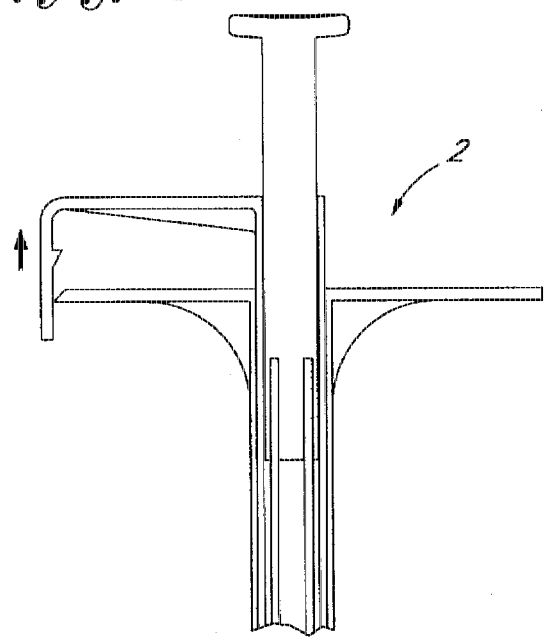
Fig. 1G
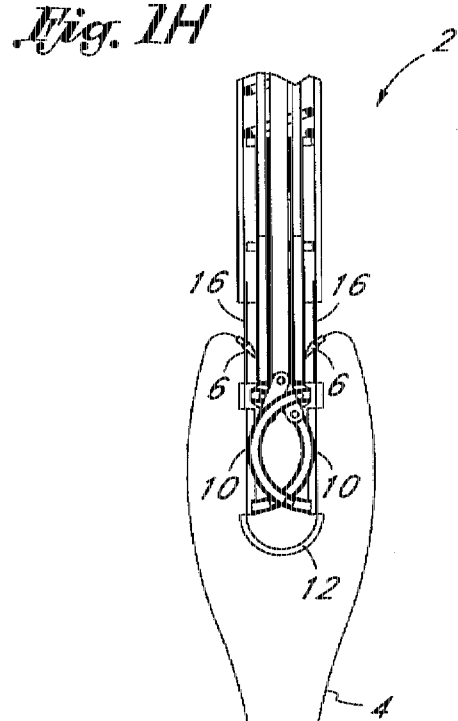
Fig. 1H
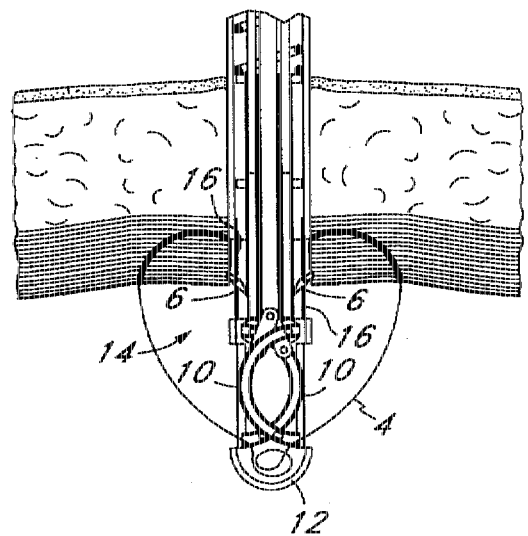
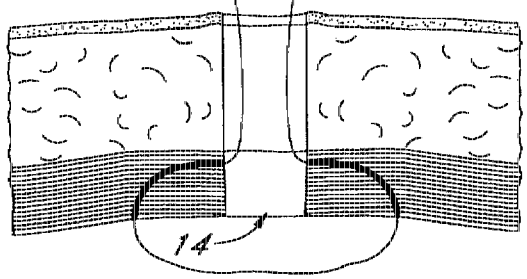

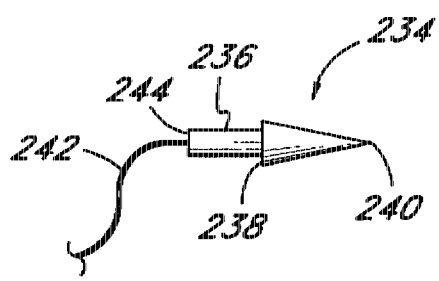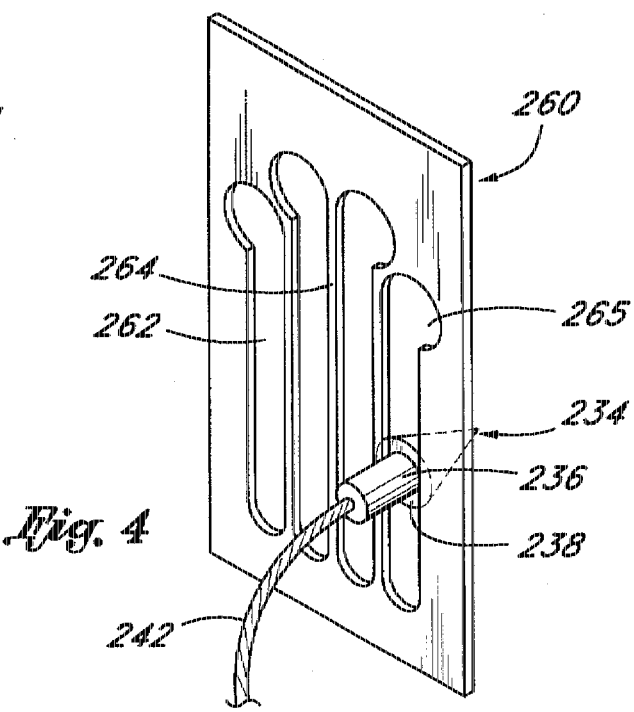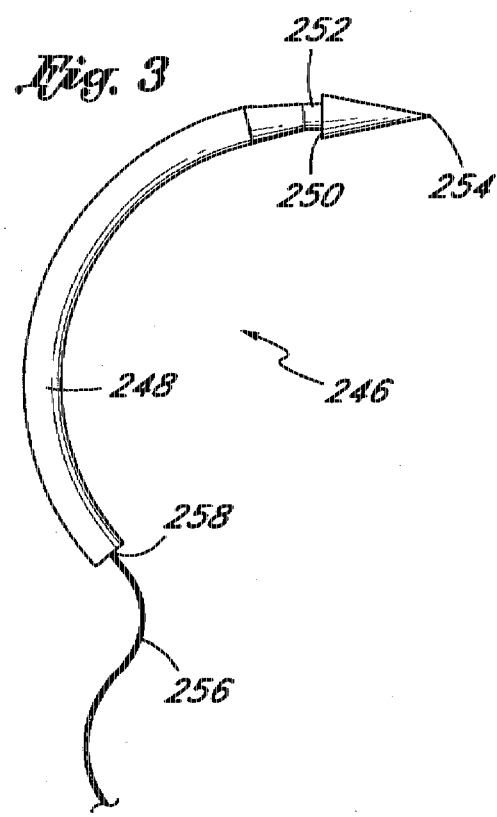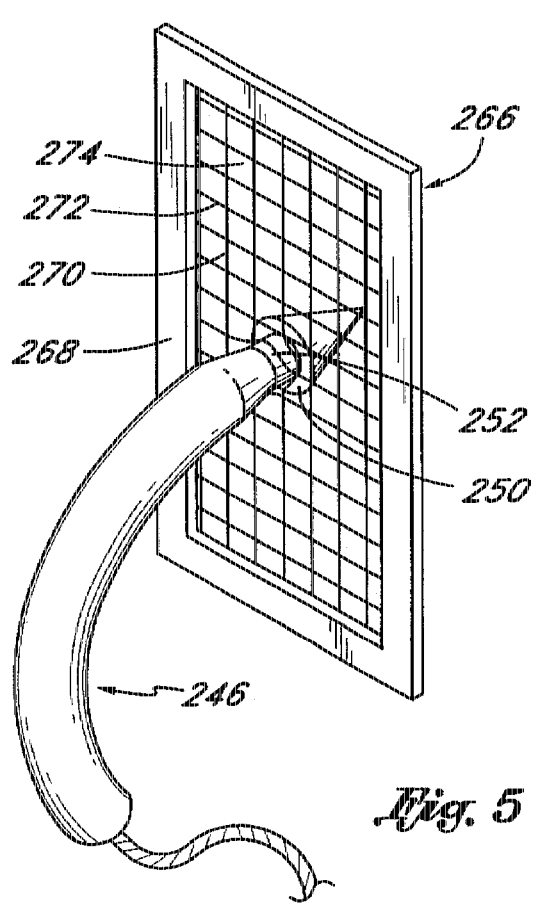

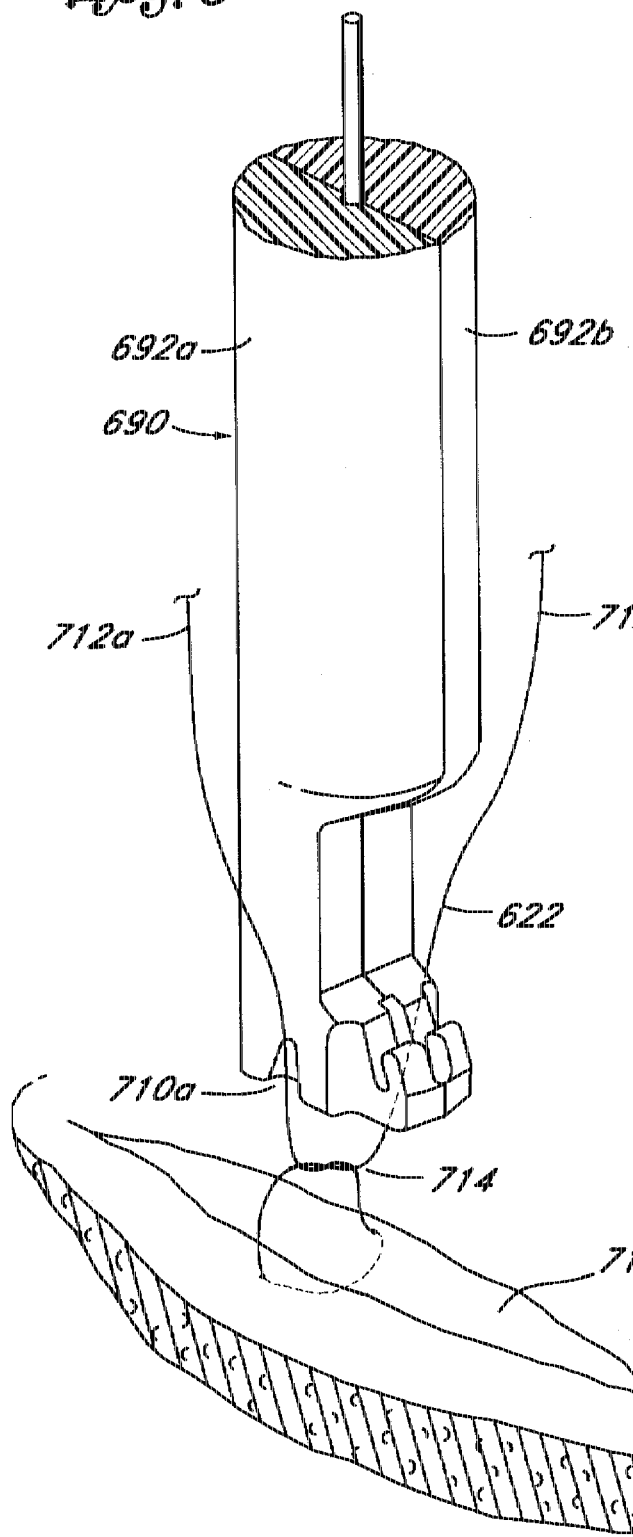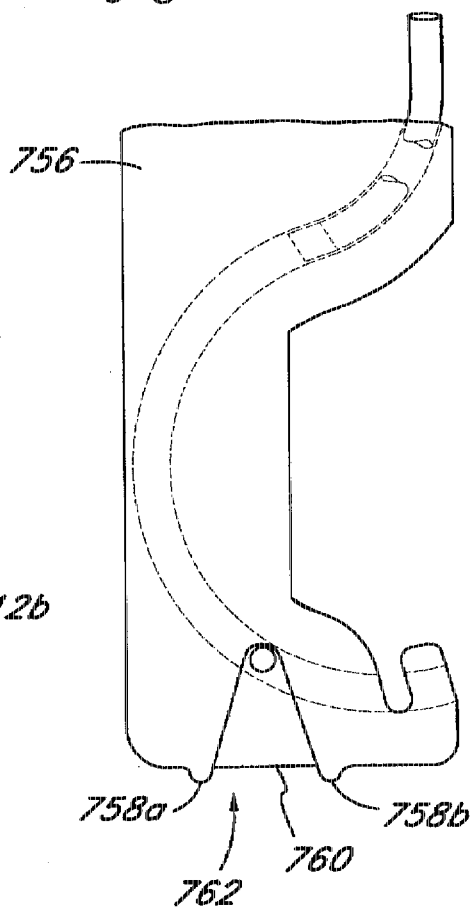

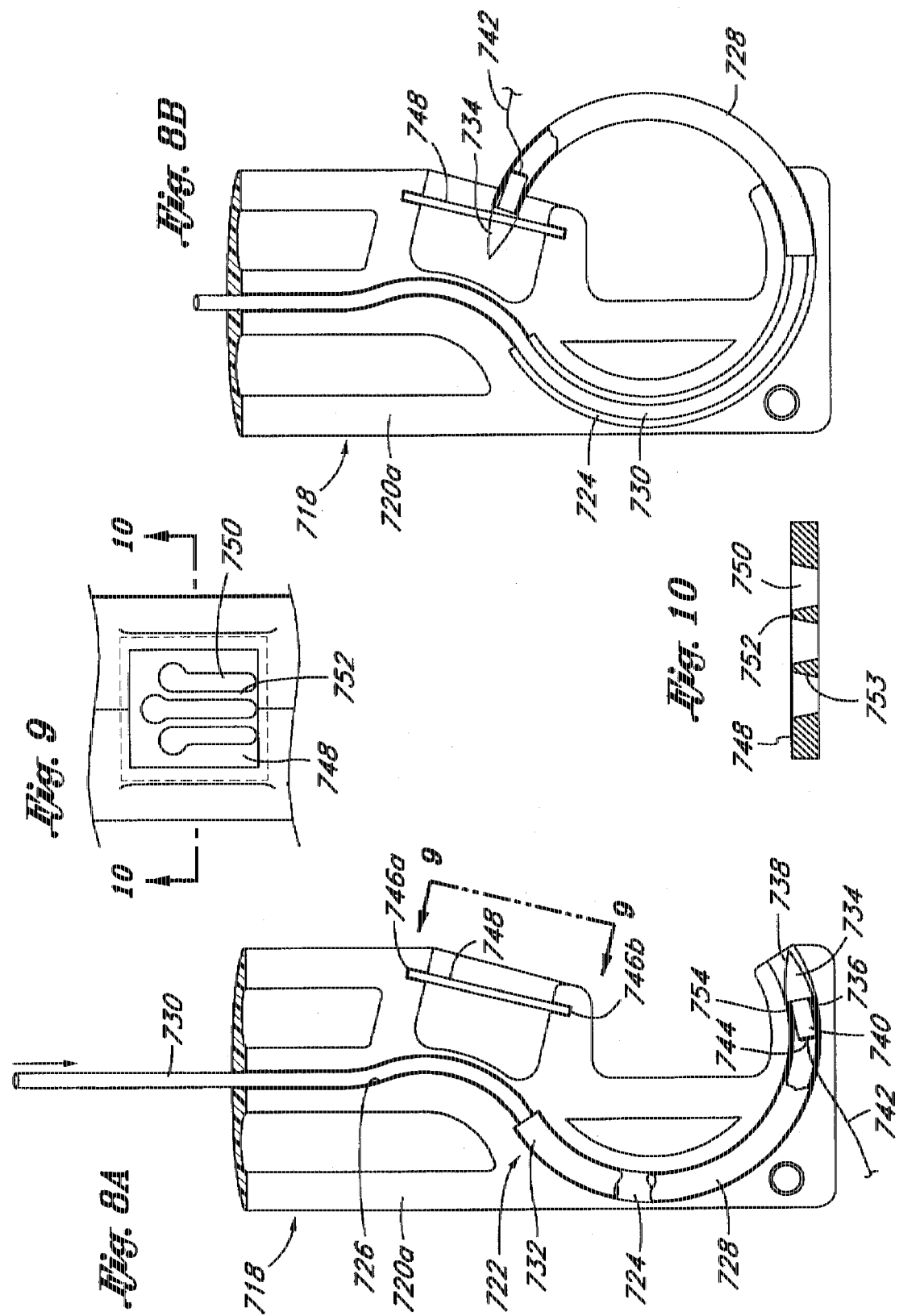

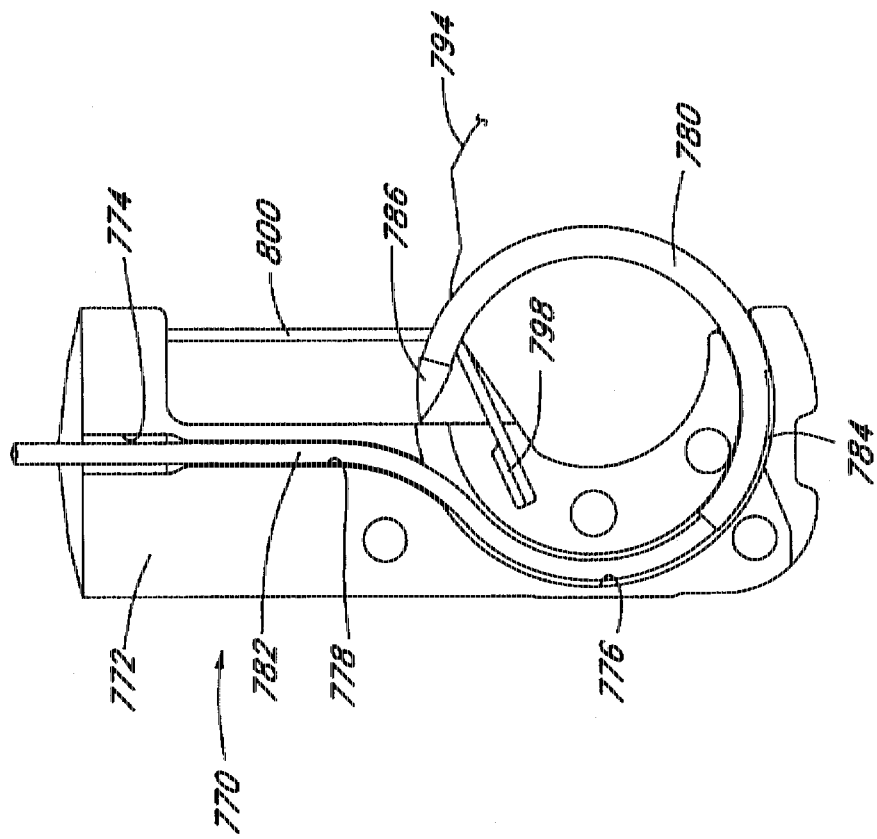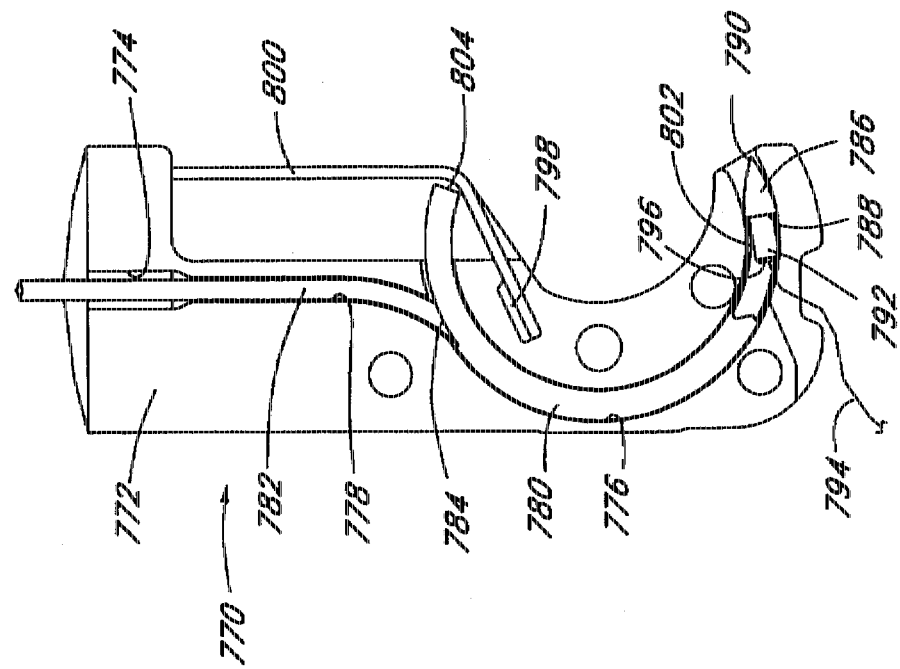

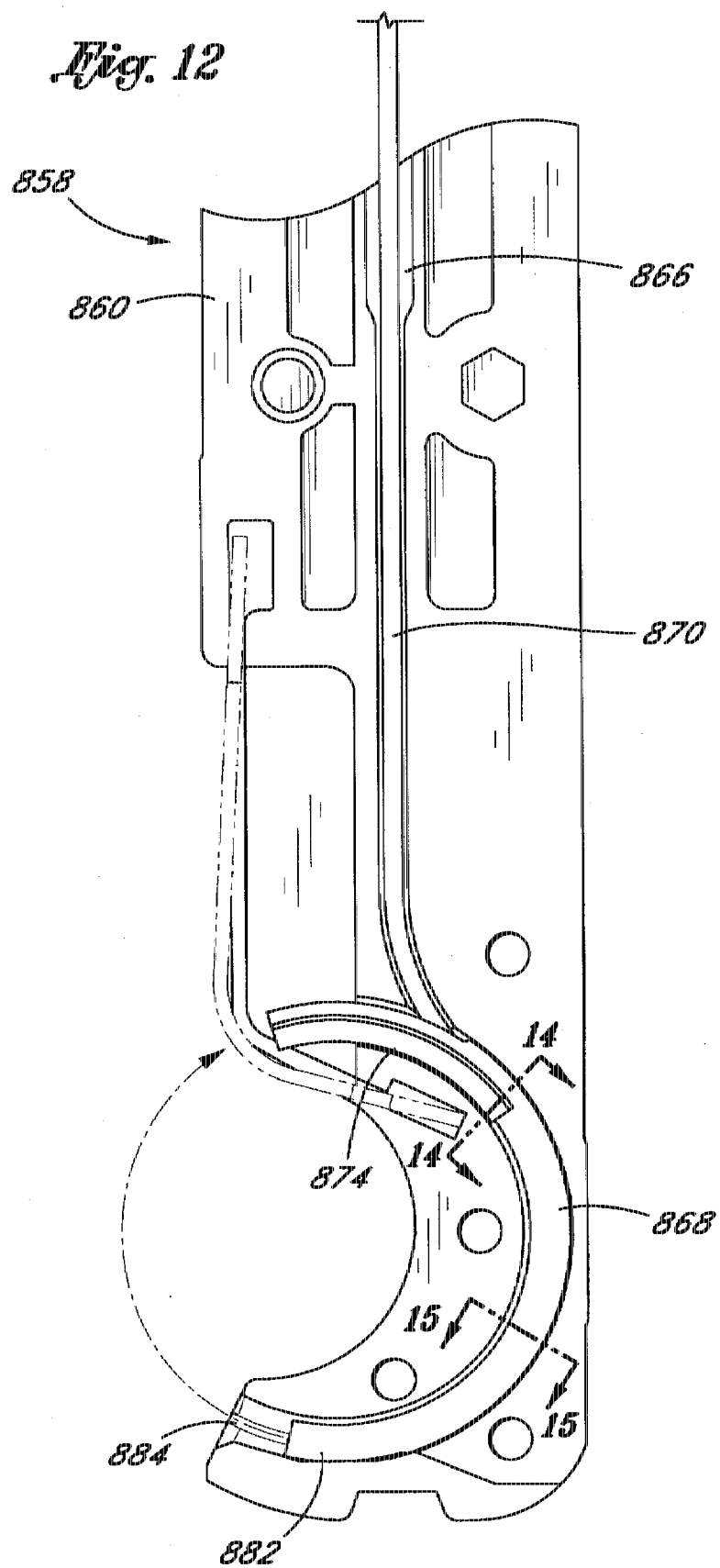

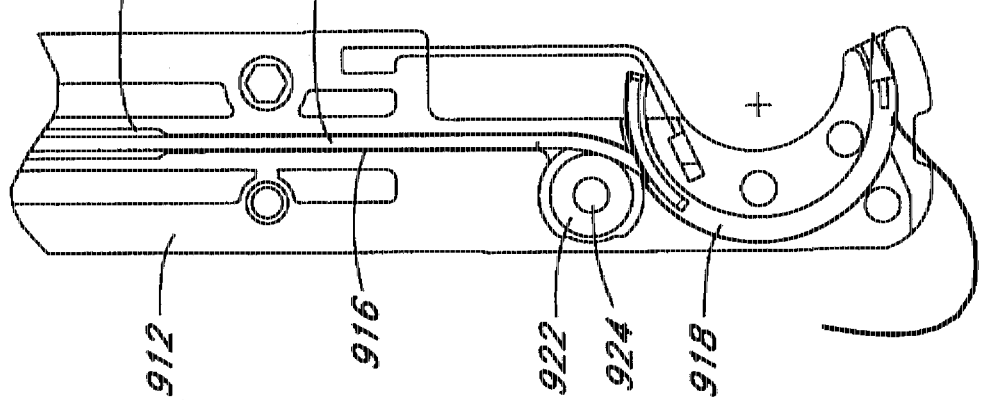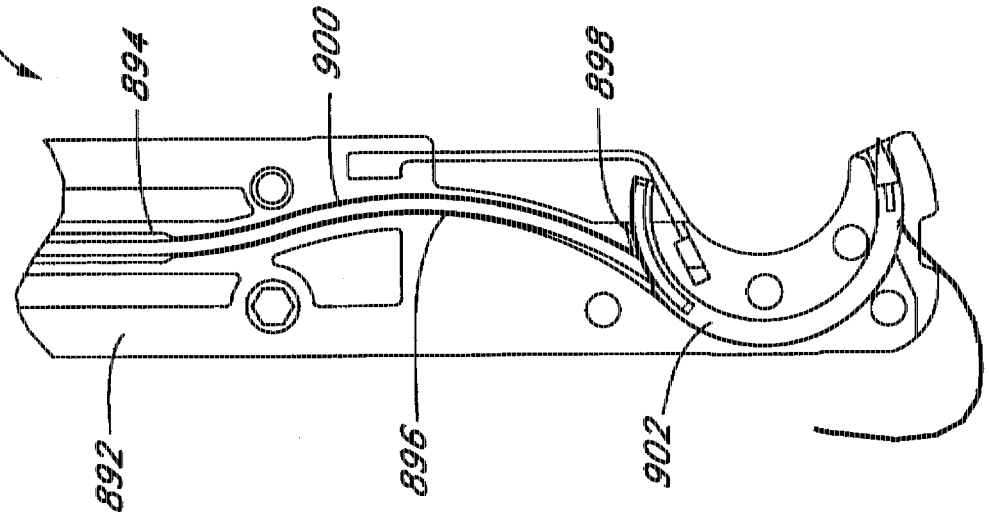

NEEDLE GUIDANCE SYSTEM FOR ENDOSCOPIC SUTURE DEVICE

RELATED APPLICATIONS

This patent application is a continuation-in-part of patent application Ser. No. 08/7311,967, now U.S. Pat. No. 5,578,044 filed Sep. 26, 1994, by inventors Norman S. Gordon and Robert P. Cooper, and entitled "Endoscopic Suture System"; which is a continuation-in-part of patent application Ser. No. 08/205,042 now U.S. Pat. No. 5,540,704, filed Mar. 2, 1994, by inventors Norman S. Gordon, Robert P. Cooper and Gordon C. Gunn, and entitled "Endoscopic Suture System", which is a continuation-in-part of patent application Ser. No. 08/057,699 now U.S. Pat. No. 5,458,609, filed May 4, 1993, by inventors Norman S. Gordon, Robert P. Cooper and Richard L. Quick, and entitled "Endoscopic Suture System" which is a continuation-in-part of patent application Ser. No. 07/941,382 now U.S. Pat. No. 5,364,408, filed Sep. 4, 1992, by inventor Norman S. Gordon, and entitled "Endoscopic Suture System". The entirety of each of the above referenced patent applications is hereby incorporated herein by reference.

FIELD OF THE INVENTION

The invention relates to devices for approximation, ligation and fixation of tissue using a suture, and particularly to the tissue separated by means of an endosurgical trocar being inserted into a body cavity, and to approximation, ligation, and fixation of tissue using endosurgical techniques and instruments.

BACKGROUND OF THE INVENTION

Suturing of body tissues is a time consuming aspect of most surgical procedures. Many surgical procedures are currently being performed where it is necessary to make a large opening to expose the area of, for instance, the human body that requires surgical repair. There are instruments that are becoming increasingly available that allow the viewing of certain areas of the body through a small puncture wound without exposing the entire body cavity. These viewing instruments, called endoscopes, can be used in conjunction with specialized surgical instrumentation to detect, diagnose, and repair areas of the body that were previously only able to be repaired using traditional "open" surgery.

In the past, there have been many attempts to simplify the surgeons' task of driving a needle carrying suture through body tissues to approximate, ligate and fixate them. Many prior disclosures, such as described in Drake et al, U.S. Pat. No. 919,138 issued Apr. 20, 1909, employ a hollow needle driven through the tissue with the suture material passing through the hollow center lumen. The needle is withdrawn leaving the suture material in place, and the suture is tied, completing the approximation. A limitation of these type of devices is that they are particularly adapted for use in open surgical procedures where there is room for the surgeon to manipulate the instrument.

Others have attempted to devise suturing instruments that resemble traditional forceps, such as Bassett, U.S. Pat. No. 3,946,740 issued Mar. 30, 1976. These devices pinch tissue between opposing jaws and pass a needle from one jaw through the tissue to the other jaw, where grasping means pull the needle and suture material through the tissue. A limitation of these designs is that they also are adapted primarily for open surgery, in that they require exposure of the tissues to be sutured in order that the tissue may be grasped or pinched between the jaws of the instrument. This is a severe limitation in the case of endoscopic surgery.

The term "endosurgery" means endoscopic surgery or surgery performed using an endoscope. In conjunction with a video monitor, the endoscope becomes the surgeons' new eyes from which they operate. Operations using an endoscope are significantly less invasive when compared to traditional open surgery. Patients usually return home the next day or in some cases the same day of the endosurgical procedure. This is in contrast to standard open surgical procedures where a large incision divides the muscle layers and allows the surgeon to directly visualize the operative area. Patients may stay in the hospital for 5 to 6 days or longer following open surgery. In addition, after endosurgical procedures, patients return to work within a few days versus the traditional 3 to 4 weeks at home following open surgery.

Access to the operative site using endosurgical or minimally invasive techniques is accomplished by inserting small tubes called trocars into a body cavity. These tubes have a diameter of, for example, between 3 mm and 30 mm and a length of about 150 mm (6 inches). There have been attempts to devise instruments and methods for suturing within a body cavity through these trocar tubes. Such an instrument is disclosed by Mulhollan et al, U.S. Pat. No. 4,621,640 issued Nov. 10, 1986. Mulhollan describes an instrument that may be used to hold and drive a needle, but makes no provision for retrieval of the needle from the body cavity, nor the completion of the suture by tying. Mulhollan's instrument is limited in that the arc through which the needle must be driven is perpendicular to the axis of the device. Another such instrument intended for endoscopic use is described by Yoon, U.S. Pat. No. 4,935,027, issued Jun. 19, 1990. This instrument uses oppositional hollow needles or tracks pushed through the tissue and coapted to create a tract through which the suture material is pushed. It is not clear how these curved tracks would be adapted to both be able to pierce the tissue planes illustrated, parallel to the tips of the tracks, and be curved toward each other to form the hollow tract.

The invention herein described may be used for final closure of umbilical and secondary trocar puncture wounds in abdominal tissues including the fascia and other layers. The umbilical puncture is routinely a puncture site of 10 mm to 12 mm. Future procedures may require trocar puncture sites up to 18 mm and greater in size. Due to the large size of the puncture wound, it is important that the site be closed or approximated at the interior abdominal wall following removal of the large trocar cannula. An improper or non existent closure can lead to a herniation of the bowel and/or bowel obstruction. The present mode for closure is to reach down to the desired tissue layer with a pair of needle drivers holding a needle and suture material and secure a stitch. Many patients are obese and present considerable fat in this region. Because the abdominal wall may be several inches thick, it is extremely difficult, tedious and time consuming to approximate the fascial tissues with a suture. Often times, following removal of a large trocar, the puncture site needs to be enlarged to accomplish this, thus negating some of the advantages of endoscopic surgery previously discussed.

One of the embodiments described herein may be of particular advantage in performing a surgery for correction of female stress incontinence, which affects over 5 million women in the United States. Stress incontinence is caused when the structures defining the pelvic floor are altered by aging or disturbed by the process of childbirth or other trauma. These structures in the pelvic floor normally hold the urinary bladder such that maintenance of a volume of urine in the bladder is accomplished by a combination of muscle tone and bladder positioning.

There are a number of surgical procedures that may be performed in order to restore the normal anatomical position of the urinary bladder. The classic open Burch suspension procedure is one such procedure and is a straightforward surgical treatment for correction of female stress incontinence. During this procedure, sutures are precisely placed in the wall of the vagina on each side of the urethra, with care being taken to avoid puncturing either the urethra or the mucosal layer of the vagina. These sutures are then looped through a ligament, called Cooper's ligament, which runs along the posterior ridge of the pubic bone. These sutures are then pulled taut, and carefully tied to suspend the urinary bladder in a more anatomically sound position, restoring normal urinary function and continence.

One of the problems with the procedure described above is that it is normally done only in conjunction with other scheduled abdominal surgical procedures such as a hysterectomy. This is because, as described earlier, an open surgical approach requiring a large abdominal incision must be used, and it is not very common for a patient to elect to have a major abdominal surgical procedure just for the treatment of incontinence.

Consequently, of late, a procedure known as a laparoscopic Burch suspension procedure has begun to find favor among physicians. The laparoscopic approach to the Burch procedure has all of the advantages described earlier with respect to post operative pain, hospital stay and recovery time. There are three difficulties associated with the laparoscopic approach; access, suture placement, and knot tying. The present invention addresses the problems surrounding the placement of the sutures in the appropriate structures and in the optimal position, and also addresses particular aspects of needle retrieval and knot tying when using endoscopic techniques.

Currently, the placement of sutures while using endoscopic techniques involves placing a semi-circular needle, attached to and carrying a suture, in a pair of endoscopic needle holders. These needle holders, which resemble a pair of pliers with an elongated shaft between the handles and the jaws, must be placed down through one of the surgical trocars into the body cavity containing the structure to be sutured. Because of their size, the needles used in these procedures are generally not able to be held in the jaws of the needle driver while being introduced through the operative trocar. The surgeon must hold the suture string in the needle holder jaws, and push the needle holder trailing the needle and suture into the body cavity. The suture and needle combination is dropped in the body cavity, and the needle is then located and picked up and properly positioned in the needle holder jaws. This is a difficult and time consuming aspect of the current endoscopic technique for suturing. The needle carrying the suture may then be driven by pronation of the wrist, causing rotation of the elongate shaft, and subsequent arcuate rotation of the semi-circular needle.

It may be seen that a limitation of this type of needle driver is that the needle may only be driven or rotated in a plane perpendicular to the axis of rotation, such axis being described by the elongate shaft and the position of the surgical trocar. Thus the current endoscopic needle drivers will not allow the surgeon to swing the needle in an arc parallel to the trocar's axis. This is a severe limitation in the case of the laparoscopic Burch, because of the orientation of the anatomy relative to the planes of access. The vaginal wall and the Cooper's ligament require the sutures to be placed in a orientation that makes the procedure extremely difficult and time consuming with the use of currently available instrumentation. It is also a limitation when attempting to ligate vessels, ligaments and other structures that run perpendicular to the axis of the operative trocar.

Another limitation of the current instrumentation is seen in the aspect that requires the surgeon to prepare the needle for penetration of the tissue while the needle is inside the body. This process is a time consuming, and sometimes frustrating exercise in hand to eye coordination, which is complicated by the fact that the surgeon is viewing the three dimensional space inside the body cavity through a two dimensional video monitor.

It may also be seen that the surgeon must be able to retrieve the needle trailing the suture material back through the same surgical trocar through which the needle driver is placed. This allows a knot to be tied in the suture outside of the body, and pushed down the trocar to the structure being sutured. Thus the needle driver must be able to retrieve the needle and bring the needle trailing the suture back up through the same trocar through which it is introduced allowing the tied knot to be pushed back down into the operative site.

It may also be seen that if the surgeon desires to place more than one suture throw through the tissue, he must be able to reload the needle into the needle driver. This may be done extracorporeally, that is, outside the body, in a manner similar to the initial loading of the suture device, or it may be done intracorporeally, that is, inside the body. Features which facilitate the intracorporeal loading of the needle can be seen to provide the surgeon with another option in the application of suture material to tissues, and could save operative time.

As it will be obvious to those skilled in the art, that the use of the techniques described above for the performance of the Burch bladder suspension procedure may be used for other endoscopic suturing tasks, such as for ligating vessels and ligaments during the performance of, for example, a hysterectomy or oophorectomy, or for the approximation of tissue flaps such as in the performance of procedures, for example, for the treatment of gastro-esophageal reflux disorder.

Currently, a number of manufacturers of suture materials and needles exist. There are USP (United States Pharmacopeia) standards for the suture material diameters and tensile strengths, however no similar standards exist for the suture needles. There are however, conventional "standard" needle sizes that many manufacturers fabricate. The needles are generally specified by the needle wire diameter, needle length and the bend arc length. A common needle size for most suture manufacturers, for example, is 26 mm long by ½ arc (180°). As it may be seen by geometric construction, a 26 mm×180° needle describes a fixed bend radius, and this nominal bend radius is fairly consistent from manufacturer to manufacturer. Typically, the suture material is crimped in either a U shaped channel formed in the distal portion of the needle, or in a drilled hole. The crimp zone size and configuration varies between manufacturers, and generally tends to straighten out the bend radius in that localized area. Between the manufacturing tolerances in the bend radius and the straightening of the end of the needle in the crimp zone, the repeatability of the shape of the needle and suture combination may vary significantly. It is therefore desirable to construct an needle guide channel which will both guide the needle precisely, and allow for the aforementioned manufacturing tolerances and perturbations. This would allow readily available commercial suture and needle combinations to be used with the suture placement system.

None of the prior art devices are adaptable to effect the placement of a suture in the anterior abdominal wall, nor are they adaptable to place sutures precisely and controllably while making provision for needle retrieval when using endoscopic techniques. It is therefore an object of the present invention to provide a family of novel suturing devices that overcomes the above set out disadvantages of prior known devices in a simple and economical manner.

It is a further object of the present invention to provide a suture device that will permit the approximation of the separated edges of a puncture wound without making a larger incision to expose the wound margins.

A further object of the present invention is to provide a suture device that will permit the surgeon to apply substantial force to the needle, permitting it to be driven through tough tissues, for example, a ligament or the abdominal fascia.

It is a further object of the present invention to provide a suture device that can be used in conjunction with modern day endoscopic surgical techniques.

Another object of the invention is to provide a suture device that will allow a needle to be driven in an arc which describes a plane parallel to the axis of the device.

Yet another object of the invention is to provide a suture device that may be used to approximate the edges of an internal wound. Another object of the present invention is to provide a suture device that permits the penetration of two needles having suture material extending there between into and through the sides of a wound and into catches thereby creating a suture loop through the wound that may be tied to approximate the tissues.

Another object of the invention is to provide a suture device that will permit the surgeon to place sutures around vessels, ligaments, and other structures to effect ligation.

SUMMARY OF THE INVENTION

The present invention is a new medical device that allows the surgeon to quickly and easily place a suture in the interior wall of a body cavity to approximate the tissues separated as a result of a puncture wound made by the introduction of a surgical trocar into a body cavity during endoscopic surgery. The invention described herein may also be used to approximate the margins of an open wound in an internal organ, such as the uterus or the stomach, such as would be effected during the course of a resection for benign or malignant lesions.

One embodiment of the present invention includes needle holders that releasably hold a pair of needles that are in turn attached to each end of a single piece of suture material. Such needle holders are held within tubular guiding tracks housed within a hollow outer sleeve that may be introduced into a puncture wound. The needle holders and guiding tracks may be deployed outside the hollow sleeve to allow the needles to engage the tissue to be approximated. A plunger is coupled to rigid driving members that are in turn attached to flexible driving members adapted to follow the shape of the guiding tracks. The flexible driving members are suitably attached to the needle holders. The plunger is pushed, simultaneously driving the needle pair into opposite sides of the puncture wound and into catches also disposed within the hollow sleeve. The needle holders are retracted into the guiding tracks, and the tracks pulled back into the hollow sleeve trailing the suture material. The device may then be withdrawn, leaving a loop of suture material precisely placed in the selected tissue, for example, in the interior wall of the body cavity. The needles are removed from the ends of the suture, and the suture material is tied to complete the approximation of the tissue.

In one aspect, the present invention differs from the prior art in that it allows a suture to be placed in a retrograde fashion in the puncture wounds created during the introduction of trocars used for endoscopic surgery. These puncture wounds have margins perpendicular to the plane of tissue dissection, unlike the wounds that are addressed by prior art in which the tissues generally overlap. Presently, all the existing instruments are designed to either approximate tissues to which direct visual and physical access may be gained during open surgery, or to approximate tissues that may be pinched between the jaws of a forceps like instrument. Wounds in body organs such as the uterus or the stomach which are created during the resection or removal of benign or malignant lesions may also have wound margins which require end to end approximation instead of overlapping. The present invention allows the surgeon to independently pass a needle through each side of the wound to allow the two sides to be drawn together, approximating the tissue.

The needle driver apparatus of the present invention may be constructed in a number of different ways. Several of the preferred ways are described herein. One embodiment uses needle guides which are semicircular in shape, holding either a semicircular needle, or a semicircular needle holder with a small needle tip. These guides are disposed across their diameter within a hollow tubular sleeve when in the retracted mode, and are rotated about one end to deploy them outside the bounds of the hollow sleeve for engaging the tissue to be sutured. The needles, or the needle holders, are driven through the tissue by axial movement of a rigid cylindrical member which contacts a flexible cylindrical member that follows the semicircular shape of the guide tracks. The needles are caught in catches placed within the hollow tubular sleeve that capture the needle by means of a leaf spring disposed to flex, preferably in one direction, and squeezing into grooves or recesses in the needles, thereby retaining the needles to the hollow tubular sleeve. The needle guides may be retracted, and the instrument removed from the wound, thus trailing the suture material. The needles are removed, the suture is tied, and the approximation is completed.

Another version of the device uses similar semicircular needle holders to the previous version, but the needle guides are eliminated. The needle holders are instead rotated about their axes such that the needles attached to the ends of the holders describe an arc that encompasses the tissue to be sutured.

It is contemplated that the above embodiments may be modified to include needle paths other than circular, such as helical, elliptical or straight, by modification of the needles, the needle holders and the needle guides. It is also possible to adapt the above configurations to allow each of the needles to be actuated and driven independently by dividing the deployment controls and the needle drivers into separate left and right hand members. Further, it is possible to utilize a tool that would use only a single needle and guide it through both sides of the wound as opposed to the double needle configuration described above.

Accordingly, another embodiment of the device uses a single needle which eliminates the deployment aspect of the needle guides. The needle guide track is incorporated directly into the cannular body which is particularly adapted for use in endoscopic procedures. The cannular body is of a diameter such that it may be placed through, for example, a standard 10 mm–12 mm trocar. The needle may be a long shouldered needle such as described previously, or may be a standard ½ circle, or 180° needle, with a length of, for example, 22 to 28 mm and crimped onto a length of standard suture material. As previously discussed, those skilled in the art will understand that various needle wire diameters, needle bend radii, needle cross sections, and suture materials are all adaptable to be used in the devices described herein. The needle may be loaded into the preformed needle guide track in the cannular body. It should be noted that the needle is placed in the cannular body across its diameter such that the point of the needle lies substantially perpendicular to the axis of the cannular body. As in previous embodiments, axial movement of a flexible drive member drives the needle out of the guiding track into and through tissue placed adjacent to the exit opening in the cannular member.

After having driven the needle into tissue, if the needle is a shouldered needle, it may be retrieved by using a keyhole shaped slot incorporated into the side of the cannular body. If the needle is a standard, non-shouldered needle, standard laparoscopic graspers, which have been introduced into the operative site via a secondary trocar, may be used to pull the needle up a short distance trailing the suture. The needle driver may then be used to retrieve the needle and suture combination by either pinching the suture material in a groove fashioned for that objective, or clamping the needle with a means adapted for that purpose. The needle trailing the suture may then be withdrawn through the surgical trocar.

This basic method of driving and retrieving the needle may be used in a number of ways at the surgeon's discretion to effect approximation, ligation, or fixation of tissue. Approximation involves the placement of one to multiple sutures in order to pull the edges of a wound together to effect healing. Ligation involves placing a suture circumferentially about a vessel or duct in order to tie it off. In the case of ligation, only a single suture is placed, and a knot tied to strangulate the encompassed structure. Fixation involves the placement of sutures to positionally secure tissues in a particular orientation, and may require that multiple sutures be placed. Fixation may also require that each end of the suture be driven through the tissue more than once.

As it may be apparent, provisions for needle retrieval, the capability of the needle to be reloaded into the needle guide track, and the positioning and orientation of the needle are important to being able to efficiently and effectively place sutures for various therapeutic reasons. The invention herein described solves these problems.

The above described embodiments may be modified to include a needle carrier adapted as described before to hold a short barbed needle. This carrier may be disposed within the preformed needle guide track in the cannular body. A similar catch mechanism as described previously is incorporated into the side of the cannular body at the end of the arcuate path described by the short needle/needle carrier combination when axial movement of the flexible drive member drives the needle and carrier combination out of the guide and through the tissue to be sutured. Use of this embodiment for closure of trocar puncture wounds can be accomplished by loading one end of a suture prepared with short needles at both ends into the needle carrier. The instrument is inserted into the puncture wound by means of the trocar placed therein. The instrument is located such that the tip of the needle is placed directly against the inside of the abdominal wall.

The needle is driven up into the abdominal fascia by the flexible needle driver coupled to the needle driver button, and into the catch. The short needle stays in the catch, the needle carrier is withdrawn back into the needle guide track, and the entire device is withdrawn from the surgical trocar. The needle is removed from the catch, the opposite end of the suture with its attached short needle is loaded into the instrument, and the entire process is repeated with the second end of the suture being driven into the tissue on the opposite side of the puncture wound, 180° from the initial stitch. The instrument and trocar are removed from the wound, and the remaining loop of suture is tied to approximate the tissues, thus closing the wound.

As it may be appreciated, this embodiment may be used in order to effect suturing in many different parts of the body, and is not limited to the closure of the wounds caused by the insertion of operative trocars into a body cavity. With the availability of both absorbable and non-absorbable suture material attached to the short needles, it is contemplated that the above described embodiment may be used in performance of procedures such as, for example, the laparoscopic Burch previously described. It is also contemplated that ligation of vessels and ligaments, such as, for instance, the ligation of uterine vessels and ligaments during the performance of a hysterectomy may be accomplished with this embodiment. This embodiment may also find application in the repair of the meniscal tissue in the knee or shoulder. It is to be clearly understood that this embodiment eliminates the manual step of needle retrieval from the wound, as the needle is automatically captured by the instrument itself.

It may be seen that for an instrument to automatically capture a needle in a consistent and repeatable fashion, it is important that the needle be guided into the catching mechanism in a predictable way. This will allow the catch to function properly, and reduces the possibility that the needle would not be engaged in the catch after being driven through tissue. It is also important that the needle drive mechanism operate with as little friction as possible, in order to allow the surgeon to have some tactile sense of the tissue being sutured.

It may also be appreciated that the limitations of the angles of access and the restrictions on the lateral manipulation of instruments used during endoscopic procedures imposed by the operative trocars can make reaching certain anatomical structures difficult. Thus, the ability to articulate an instrument within the body cavity independent of the manipulation of the main body shaft can be of particular advantage in accessing these difficult to reach structures. By articulating the head of the needle driver instrument, the exit angle of the needle may be adjusted, as well as opening the possibility of accessing certain areas of the body which are inaccessible in a linear fashion due to the aforementioned mechanical constraints.

In a first embodiment, the present invention is a suturing instrument comprising: an elongate body member having a longitudinal axis; a needle deployment system located within a distal end portion of the elongate body member, the needle deployment system comprising: a curved needle carrier channel having a guide groove formed therein; a curved needle carrier movably positioned in the curved needle carrier channel, the curved needle carrier having a guide wing which engages the guide groove formed in the curved needle carrier channel thereby guiding and stabilizing the curved needle carrier within the curved needle carrier channel; and a deployment controller having a proximal end, a distal end, a retracted position and a deployed position, the deployment controller extending substantially along the longitudinal axis of the elongate body member to the distal end of the elongate body member where it is coupled to the curved needle carrier and moves the curved needle carrier through the curved needle carrier channel as it moves between the retracted position and the deployed position. The deployment controller may further comprise an internal driver pathway extending from a proximate end portion of the elongate body member to the distal end portion of the elongate body member, wherein the internal driver pathway may comprise a curved pathway section near the distal end portion of the elongate body member, the curved pathway section having a distal end curvature which defines a distal end tangent line. This embodiment may further comprise a channel intersection where the distal end of the curved pathway section joins the curved needle carrier channel, wherein: the curved needle carrier channel has a curvature at the channel intersection which defines a curved needle channel intersection tangent line; and the curved pathway section distal end tangent line and the curved needle carrier channel intersection tangent line are substantially parallel at the channel intersection. The deployment controller may further comprise a flexible driver member coupled to the curved needle carrier, the flexible driver member being slidably disposed in the curved pathway section of the internal driver pathway. In some embodiments, the flexible driver member further comprises an alloy of nickel and titanium. In other embodiments, the curved needle carrier guide wing further comprises a plurality of pins. This embodiment may further comprise a rolling bearing member positioned adjacent the curved pathway section of the internal driver pathway and the channel intersection such that the flexible driver member contacts the rolling bearing member.

In a second embodiment, the present invention is a suturing instrument comprising: an elongate body member having a longitudinal axis; a curved needle carrier channel positioned in the elongate body member wherein the curved needle carrier channel has a guide groove formed therein; and a curved needle carrier movably positioned in the curved needle carrier channel, the curved needle carrier having a guide wing which engages the guide groove formed in the curved needle carrier channel thereby guiding and stabilizing the curved needle carrier within the curved needle carrier channel. This embodiment may further comprise an internal driver pathway extending from a proximate end portion of the elongate body member to a distal end portion of the elongate body member, wherein the internal driver pathway comprises a curved pathway section near the distal end portion of the elongate body member, the curved pathway section having a distal end curvature which defines a distal end tangent line. This embodiment may further comprise a channel intersection where the distal end of the curved pathway section joins the curved needle carrier channel, wherein: the curved needle carrier channel has a curvature at the channel intersection which defines a curved needle channel intersection tangent line; and the curved pathway section distal end tangent line and the curved needle carrier channel intersection tangent line are substantially parallel at the channel intersection. Additionally, this embodiment may further comprise a flexible driver member coupled to the curved needle carrier, the flexible driver member being slidably disposed in the curved pathway section of the internal driver pathway. The flexible driver member may further comprise an alloy of nickel and titanium. In some embodiments, the curved needle carrier guide wing further comprises a plurality of pins. This embodiment may further comprise a rolling bearing member positioned adjacent the internal driver pathway and the channel intersection such that the flexible driver member contacts the rolling bearing member.

In another aspect, the present invention is a method of stabilizing and guiding a curved needle carrier movably positioned in a curved needle carrier channel, the method comprising: providing a guide groove in the curved needle carrier channel; providing a guide wing on the curved needle carrier; and positioning the curved needle carrier within the curved needle carrier channel such that the guide wing on the curved needle carrier slidably engages the guide groove in the curved needle carrier channel.

In a third embodiment, the present invention is a suturing instrument comprising: an elongate body member; a curved tubular channel positioned in a distal end portion of the body member, wherein the curved tubular channel further comprises: a length defined by a proximate end and a distal end; and a bearing groove formed along at least a portion of the curved tubular channel length; and a curved needle carrier movably positioned in the curved tubular channel, the curved needle carrier having a bearing wing which engages the bearing groove formed in the curved tubular channel thereby guiding and stabilizing the curved needle carrier movably positioned within the curved tubular channel. This embodiment may further comprise an internal driver pathway extending from a proximate end portion of the elongate body member to a distal end portion of the elongate body member, wherein the internal driver pathway comprises a curved pathway section near the distal end portion of the elongate body member, the curved pathway section having a distal end curvature which defines a distal end tangent line. This embodiment may further comprise a channel intersection where the distal end of the curved pathway section joins the curved tubular channel, wherein: the curved tubular channel has a curvature at the channel intersection which defines a curved tubular intersection tangent line; and the curved pathway section distal end tangent line and the curved tubular channel intersection tangent line are substantially parallel at the channel intersection. Additionally, this embodiment may further comprise a flexible driver member coupled to the curved needle carrier, the flexible driver member being slidably disposed in the curved pathway section of the internal driver pathway. The flexible driver member may further comprise an alloy of nickel and titanium. In some embodiments, the curved needle carrier bearing wing further comprises a plurality of pins. In another aspect, this embodiment further comprises a rolling bearing member positioned adjacent the internal driver pathway and the channel intersection such that the flexible driver member contacts the rolling bearing member.

In a fourth embodiment, the present invention is a suturing instrument comprising: an elongate body member having a longitudinal axis; an internal driver pathway extending from a proximate end portion to a distal end portion of the elongate body member, wherein the internal driver pathway comprises a curved pathway section near the distal end portion of the elongate body member, the curved pathway section having a distal end curvature which defines a distal end tangent line; a curved needle carrier channel located near the distal end portion of the elongate body member; and a channel intersection where the distal end of the curved pathway section joins the curved needle carrier channel, wherein: the curved needle carrier channel has a curvature at the channel intersection which defines a curved needle channel intersection tangent line; and the curved pathway section distal end tangent line and the curved needle carrier channel intersection tangent line are substantially parallel at the channel intersection. This embodiment may further comprise a flexible driver member coupled to the curved needle carrier, the flexible driver member being slidably disposed in the curved pathway section of the internal driver pathway. The flexible driver member may further comprise an alloy of nickel and titanium. In some embodiments, the curved needle carrier guide wing further comprises a plurality of pins. In another aspect, this embodiment may further comprise a rolling bearing member positioned adjacent the curved pathway section of the internal driver pathway and the channel intersection such that the flexible driver member contacts the rolling bearing member.

In a fifth embodiment, the present invention is a suturing instrument comprising: an elongate body member having a longitudinal axis; a curved needle carrier channel having a guide track formed therein, the curved needle carrier located within the elongate body member at a distal end thereof, the curved needle carrier channel located substantially in a plane which is substantially parallel to the elongate body member longitudinal axis, the curved needle carrier channel forming a needle exit port in a side wall of the elongate body member; and a curved needle carrier movably positioned in the curved needle carrier channel, the curved needle carrier having a guide wing which engages the guide track formed in the curved needle carrier channel thereby guiding and stabilizing the curved needle carrier within the curved needle carrier channel. This embodiment may further comprise an internal driver pathway extending from a proximate end portion of the elongate body member to a distal end portion of the elongate body member, wherein the internal driver pathway comprises a curved pathway section near the distal end portion of the elongate body member, the curved pathway section having a distal end curvature which defines a distal end tangent line. This embodiment may further comprise a channel intersection where the distal end of the curved pathway section joins the curved needle carrier channel, wherein: the curved needle carrier channel has a curvature at the channel intersection which defines a curved needle channel intersection tangent line; and the curved pathway section distal end tangent line and the curved needle carrier channel intersection tangent line are substantially parallel at the channel intersection. Additionally, this embodiment may further comprise a flexible driver member coupled to the curved needle carrier, the flexible driver member being slidably disposed in the curved pathway section of the internal driver pathway. The flexible driver member may further comprise an alloy of nickel and titanium. In some embodiments, the curved needle carrier guide wing further comprises a plurality of pins. Another variation of this embodiment further comprises a rolling bearing member positioned adjacent the internal driver pathway and the channel intersection such that the flexible driver member contacts the rolling bearing member.

These and other characteristics of the present invention will become apparent through reference to the following detailed description of the preferred embodiments and accompanying drawings.

BRIEF DESCRIPTION OF THE DRAWINGS

FIGS. 1A through 1H illustrate the general structure and operation of a first embodiment of the present invention.

FIG. 2 is a detail plan view of a needle.

FIG. 3 is a detail plan view of an alternate needle.

FIG. 4 is a detail perspective view of a catch mechanism with a needle.

FIG. 5 is a detail perspective view of an alternate catch mechanism with a needle.

FIG. 6 is a detailed perspective view of the end of a suturing device illustrating its use for pushing knots tied in suture.

FIG. 7 is a detailed plan view of an alternate embodiment of a suture device illustrating features for use for pushing knots tied in suture.

FIGS. 8A and 8B are detailed cross sectional views illustrating the general structure and operation of an alternate embodiment of a needle delivery and capture system.

FIGS. 8C and 8D are detailed cross sectional views illustrating the general structure and operation of another alternate embodiment of a needle delivery and capture system.

FIG. 9 is a projected detail view taken along the lines of view 9—9 of FIG. 8A illustrating the needle catch.

FIG. 10 is a cross sectional view taken along the lines of 10—10 on FIG. 9.

FIG. 12 is a detailed cross sectional view illustrating the relationship between the needle carrier and guide track.

FIG. 16 is a detailed cross sectional view illustrating the general structure of an alternate embodiment of a needle delivery and capture system.

FIG. 17 is a detailed cross sectional view illustrating the general structure of an alternate embodiment of a needle delivery and capture system.

DETAILED DESCRIPTION OF THE PREFERRED EMBODIMENTS

Figure 11:
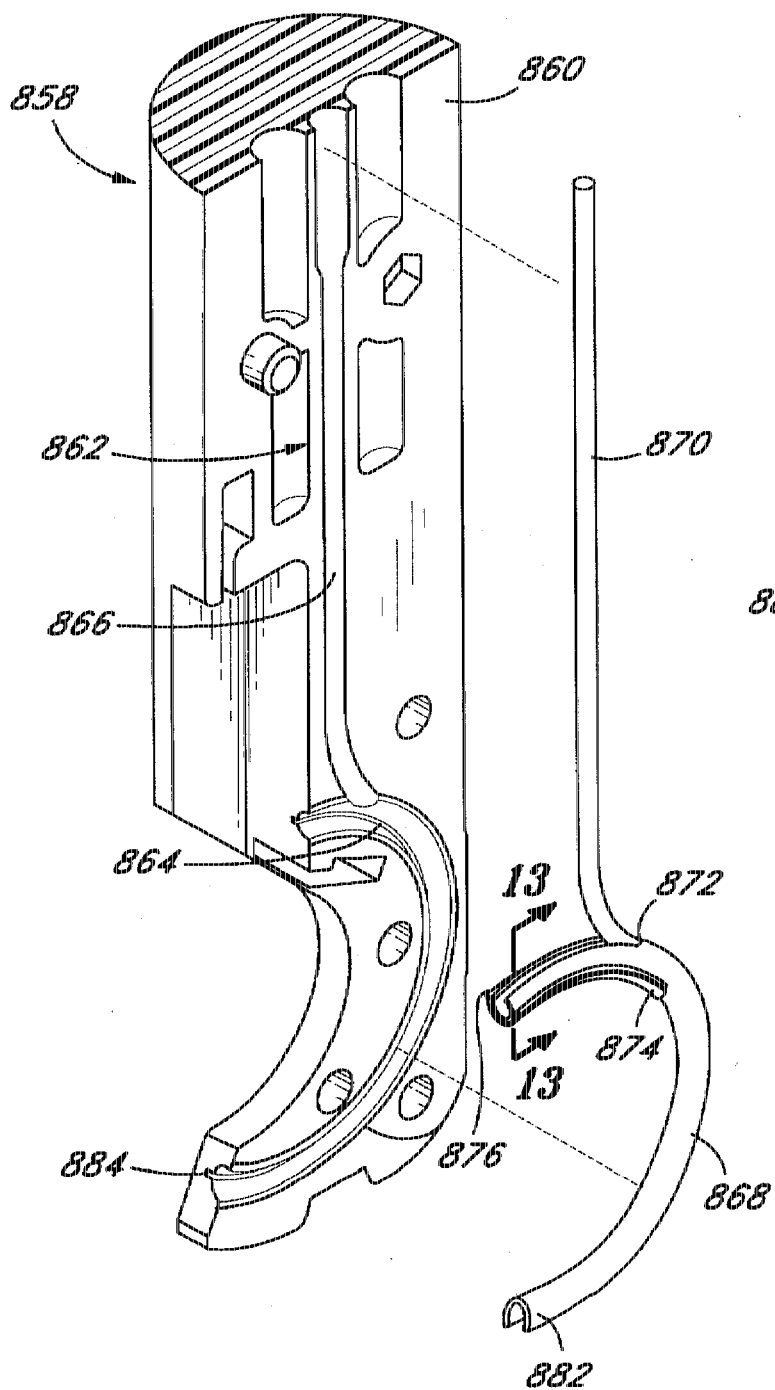
FIG. 11 is a detailed perspective view illustrating the general structure of an alternate embodiment of the needle carrier and guide track.

Although the principles of the present invention are applicable to any device suitable for use in surgical procedures, whether performed on humans or animals, particular utility is effected in human abdominal surgery performed using endoscopic techniques for closure of the wounds created during the introduction of trocars into the abdominal cavity, and particularly the puncture wounds created thereof, as well as closure or approximation of the wounds created either during the resection of benign or malignant lesions, or during the performance of other therapeutic procedures on an organ or organs within a body cavity.

FIGS. 1A through 1H illustrate the general structure and operation of a first embodiment of the present invention. FIGS. 1A and 1B show a device 2, according to the present invention, which incorporates a length of standard suture material 4 with a needle 6 on each end. The needles 6 are held by a needle carrier 8 (FIG. 1D) and loaded into two guiding tracks 10. The guiding tracks 10, containing the needle carriers 8 and needles 6, are deployable outside a housing 12 of the device 2 to allow the suture material 4 to be placed outside the limits of a puncture wound 14 (FIGS. 1B and 1C). After deployment of the guiding tracks 10 (with the needle carriers 8 and needles 6 contained within) the needle carriers 8 and needles 6 are driven out of the guiding tracks 10 and into tissue surrounding the puncture wound 14 (FIGS. 1C and 1D). The needles 6 are driven into a catch mechanism 16 (FIG. 1D). The needle carriers 8 are retracted back into the guiding tracks 10 (FIG. 1E). The guiding tracks 10 (now containing only the needle carriers 8 without the needles 6) and the catch mechanism 16 with the captured needles 6, are retracted as shown in FIGS. 1F, 1G and 1H. With a loop of suture 4 having thus been placed in the tissue surrounding the puncture wound 14, the suture device 2 is removed from the wound 14, thereby pulling the ends of the suture 4 with it (FIG. 1H). Closure of the puncture wound 14 is accomplished by cutting the suture 4 to remove the needles 6, tying a knot in the suture 4, and pushing it into the wound 14. Superficial closure is then performed by normal means according to the surgeon's preference.

FIGS. 2 and 3 show detail plan views of alternate needle embodiments. Referring to FIG. 2, a needle 234 comprises a body 236, and a shoulder 238 tapering to a point 240. A length of suture material 242 is inserted into a hole 244 and attached to the needle 234 thereby. Referring now to FIG. 3, a needle 246 comprises a body 248 and a shoulder 250 formed by a groove 252 which tapers to a point 254. A length of suture material 256 is inserted into a hole 258 and attached to the needle 246 thereby.

FIGS. 4 and 5 show detail perspective views of alternate catch embodiments and illustrate their operation. A catch 260 is preferably constructed of thin stainless steel of high temper, such as ANSI 301 full hard. Although the catch 260 may be fabricated by means of stamping or laser machining, the preferred method is by chemical etching. Referring to FIG. 4, the catch 260 includes openings 262 defined by ribs 264. As the needle 234 enters the opening 262, the ribs 264 deflect slightly to allow the shoulder 238 to pass through. After the shoulder 238 has passed the ribs 264, the ribs spring back to their original position defining the openings 262. The openings 262 are chosen to be smaller in dimension than the shoulder 238. This causes the catch 260 to retain the needle 234 by the interference between the shoulder 238 and the ribs 264 around the body 236. When it is necessary to remove the needle 234 from the catch 260, it may be moved toward an opening 265 which is sized to allow the needle shoulder 238 to pass through without resistance.

Referring now to FIG. 5, a catch 266 includes a frame 268 to which is attached a woven mesh 270. Threads 272 creating the woven mesh 270 may be made out of nylon or polyester or the like woven in a common over/under pattern. The weaving of the threads 272 creates holes 274 in the mesh through which a needle 246 may be passed. The needle 246 is constructed such that the shoulder 250 defined by the groove 252 is larger than the holes 274, or conversely, the holes 274 are chosen to be smaller than the shoulder 250. The point 254 of the needle 246 pushes the threads 272 aside creating room for the shoulder 250 to pass through the holes 274. As the threads 272 return to their original positions, the catch 266 holds onto the needle 246 by means of the mismatch in the size of the holes 274 and the shoulder 250.

It may be seen and should be understood that catches 260 and 266 are capable of catching either needle 234 or 246. The examples of needle 234 coupled with catch 260 and needle 246 coupled with catch 246 are given purely to illustrate the concepts of each embodiment and do not exclude their coupling with alternate designs.

As previously mentioned, in order to complete any suturing application, a knot must be tied to secure the suture material to the tissue. We now describe a simple means for facilitating the tying of knots during endoscopic procedures. Referring to FIG. 6, there is seen a suture applicator tip 690 which includes housing halves 692a,b. At the distal end of the suture applicator tip 690 are concave recesses 710a,b. The suture 622 includes ends 712a,b and a knot 714, and passes through tissue 716. It is to be understood that the suture applicator tip 690 has been passed into an interior body cavity, such as the abdominal cavity, through a surgical trocar. The knot 714 in the suture 622 has been tied extracorporeally, i.e. external to the body cavity, and with the use of the suture applicator tip 690, has been guided through the surgical trocar by the concave recesses 710 to the position shown in FIG. 6. The user, by keeping tension on the ends 712a,b of the suture 622, and by pushing on the suture applicator tip 690, may guide the knot 714 further down to the tissue 716. To complete the tying of a knot, the suture applicator tip 690 is removed from the surgical trocar and another loop or knot is tied extracorporeally, and pushed down the surgical trocar in like manner to that described above. Thus it may be seen that the present invention may be used to drive the needle, retrieve the needle from the tissue, and facilitate the placement of knots to complete the approximation, ligation, or fixation.

An alternate embodiment of the knot pusher may be seen by referring to FIG. 7. There may be seen a cannular body 756 which includes protrusions 758a,b and a land 760. The protrusions 758a,b and the land 760 combine to form a pocket 762, which may function in a similar manner to the concave recesses 710 described in FIG. 6. It should thus be clear that guidance of the suture for the purposes of knot tying may be accomplished by means of either a pocket formed by protrusions or other positive external features such as ribs or bumps on the end of the cannular body, or by recesses or other negative external features such as depressions, concavities, or reliefs formed in the end of the cannular body.

Yet another embodiment of the invention is an alternate needle driver and catch system as shown in FIG. 8A and FIG. 8B, which are detailed cross sectional views of the distal end of the suture application system. Referring to FIG. 8A an elongate cannular body 718 is comprised of the housing halves 720a,b. It is to be understood that for clarity only one of the housing halves 720 of the cannular body 718 is shown in FIG. 8A and FIG. 8B. The housing halves 720 are configured to create a guided pathway 722 which is comprised of a needle carrier guide track 724 and a flexible carrier driver guide track 726. A needle carrier 728 and flexible carrier driver 730 are joined at an end 732 of the needle carrier 728. The attachment between the needle carrier 728 and the flexible carrier driver 730 at the end 732 can be accomplished by crimping, welding, adhesive bonding or various other techniques. A bullet needle 734 includes a shoulder 736, a point 738 and a shaft 740. A length of suture material 742 is attached to the shaft 740 by placing it in a hole 744 and holding it there by suitable means, such as crimping or adhesive bonding or the like. Further incorporated in the housing halves 720 are catch pockets 746a,b which position and retain a needle catch 748. Referring to FIG. 9, which is a detail plan view taken along the lines of 9—9 of FIG. 8A, it may be seen that the needle catch 748 includes openings 750 defined by ribs 752. The configuration and function of the needle catch 748 is similar to that described earlier in FIG. 4. The bullet needle 734 is inserted into an end 754 of the needle carrier 728. The shoulder 736 of the bullet needle 734 rests on the end 754 of the needle carrier 728, the end 754 dimensioned to hold and retain the bullet needle 734 in a manner previously described. When the catch 748 is fabricated by means of chemical etching, the most preferred method is to etch from a single side, known in the art as single sided etching. When the catch 748 is etched from a single side, the ribs 752 have a tapered cross section 753 as shown in FIG. 10, which is a detail cross sectional view taken along the lines of 10—10 of FIG. 9. The tapered cross section 753 helps to guide the needle 734 into the catch openings 750, minimizing the chance of the needle 734 hitting the top of the ribs 752.

Referring now to FIGS. 8A and 8B, the operation of this embodiment will be described. It is to be understood that the function of this embodiment is similar to that previously described in FIGS. 1A through 1H, that is, to approximate and close the puncture wounds created when surgical trocars are introduced into a body cavity. For clarity, the imposition of tissue planes along the path of needle travel to be described in FIGS. 8A and 8B has not been shown, although it is implied. FIG. 8A shows the bullet needle 734 loaded into the needle carrier 728 which is depicted in the retracted position. In this position, the cannular body 718 may be passed through a surgical trocar and into a body cavity for operation of the device. As shown in FIG. 8B, as the flexible carrier driver 730 is advanced into the needle carrier guide track 724, the needle carrier 728, holding the bullet needle 734 and trailing the suture 742 is driven on a semi-circular path terminating in the needle catch 748. The bullet needle 734 is captured by the catch 748 in a manner previously described in FIG. 4. The flexible carrier driver 730 may be retracted back into the flexible carrier driver guide track 726, causing the needle carrier 728 to rotate back into the needle carrier guide track 724 in the body half 720. The instrument may be removed from the surgical trocar, and the process repeated on the other side of the wound, and after knots have been tied, an approximation of the puncture wound is accomplished. It may be seen that a knot pusher such as that described in FIG. 6 may be incorporated into the distal end of this embodiment of the suture applicator to effect the tying of knots for approximation of the puncture wounds. As such, the knots would be pushed directly into the wound, and not necessarily through the surgical trocar.

Yet another embodiment of the invention is an alternate needle driver and catch system as shown in FIG. 8C and FIG. 8D, which are detailed cross sectional views of the distal end of a suture application system and are similar in construction to those already described in FIGS. 8A and 8B. Referring to FIG. 8C, an elongate cannular body 770 is comprised of housing halves 772a,b. It is to be understood that for clarity only one of the housing halves 772 of the cannular body 770 is shown in FIG. 8C and FIG. 8D. The housing halves 772 are configured to create a guided pathway 774 which is comprised of a needle carrier guide track 776 and a flexible carrier driver guide track 778. A needle carrier 780 and flexible carrier driver 782 are joined at saddle 784 of the needle carrier 780. The saddle 784 comprises a channel, groove or opening formed in the proximate end of the needle carrier 780 into which the flexible carrier driver 782 may enter circumferentially as opposed to axially. The attachment between the needle carrier 780 and the flexible carrier driver 782 at the saddle 784 can be accomplished by crimping, welding, adhesive bonding or various other techniques. A bullet needle 786 includes a shoulder 788, a point 790 and a shaft 792. A length of suture material 794 is attached to the shaft 792 by placing it in a hole 796 and holding it there by suitable means, such as crimping or adhesive bonding or the like. Further incorporated in the housing halves 772 are catch pockets 798a,b which position and retain a needle catch 800. The configuration and function of the needle catch 800 is similar to that described earlier in FIG. 4. The bullet needle 786 is inserted into an end 802 of the needle carrier 780. The shoulder 788 of the bullet needle 786 rests on the end 802 of the needle carrier 780, the end 802 dimensioned to hold and retain the bullet needle 786 in a manner previously described.

Although the operation of this embodiment is virtually identical to that described in FIGS. 8A and 8B, there are improvements included in this embodiment to the overall operation of the suture system. Referring back to FIGS. 8A and 8B, as it may be appreciated, as the needle carrier 728 approaches the end of its stroke, as illustrated in FIG. 8B, the circumferential length of the needle carrier 728 left inside the needle carrier guide track 724 is quite minimal. This can allow the needle carrier 728 holding the needle 734 to drift off of the predescribed arcuate path which terminates in the needle catch 748. This drift may allow the needle 734 to miss the catch 748, causing an incomplete suturing cycle. It is desirable, then, to increase the circumferential length of the needle carrier left inside the guide track in order to improve the guidance of the needle carrier.

Accordingly, the embodiment illustrated in FIGS. 8C and 8D shows the needle carrier 780 with the saddle 784. The saddle 784 allows the flexible carrier driver 782 to exit from the needle carrier 780 at a point along the circumference, rather than at a distal end 804. This may be seen to increase the overall arc length of the needle carrier 780 when compared with the needle carrier 728 shown in FIG. 8A. As a result, when the flexible carrier driver 782 is slidably moved in the guided pathway 774, and the needle carrier 780 is caused to rotate within the needle carrier guide track 776, it may be seen by referring to FIG. 8D that when the bullet needle 786 enters the needle catch 800, a significantly larger portion of the needle carrier 780 is still captured within the needle carrier guide track 776. This may be seen to provide additional guidance to the needle carrier 780 as it penetrates tissue. It may also be seen that the geometry described above allows for a longer stroke length, and therefor greater tissue bite.

As it may be appreciated by those skilled in the art, during the performance of a surgical procedure where suturing of body tissues is required, it is often necessary to lift or twist the tissue planes with the needle in order to approximate them in their final positions. This lifting and/or twisting can place significant stresses on the needle, and indeed, breakage of needles in the operative field is a fairly common event. In the embodiments just described, the "needle" is the combination of, for example in FIG. 8C, the needle carrier 780 and the bullet needle 786. In this example, the majority of the induced stresses are absorbed by the needle carrier 780. In addition to provisions for leaving a more substantial portion of the needle carrier in the guide track for additional guidance, FIGS. 11 through 15 now describe an alternate embodiment of the needle carrier and guide track which further improves the guidance and resistance to deflection due to the stresses just described.

Referring now to FIG. 11, there may be seen the distal end of an elongate cannular body 858 which is comprised of housing halves 860a,b. It is to be understood that for clarity only one of the housing halves 860 of the cannular body 858 is shown in FIG. 11. The housing halves 860 are configured to create a guided pathway 862 which is comprised of a needle carrier guide track 864 and a flexible carrier driver guide track 866. A needle carrier 868 includes a saddle 872, to which is attached a carrier bearing 874. The saddle 872 comprises a channel, groove or opening formed in the proximate end of the needle carrier 868 into which the flexible carrier driver 870 may enter circumferentially as opposed to axially. That is, at the intersection of the flexible carrier driver guide track 866 and the needle carrier guide track 864, lines which are tangent to the flexible carrier driver guide track 866 and the needle carrier guide track 864 are substantially parallel.

Figure 13A:
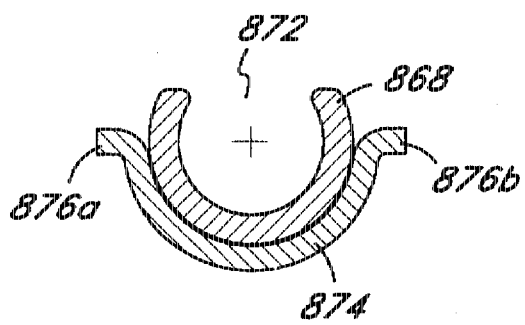
FIGS. 13A and 13B are cross sectional views of two alternate designs of the needle carrier taken upon the lines of 13—13 on FIG. 11.

The construction of the needle carrier may be best understood by referring to FIG. 13A, where a cross sectional view shows the needle carrier 868 and the carrier bearing 874. The carrier bearing 874 further includes bearing wings 876a,b. The carrier bearing 874 may be joined by welding, adhesive bonding or the like to the needle carrier 868.

Figure 13B:
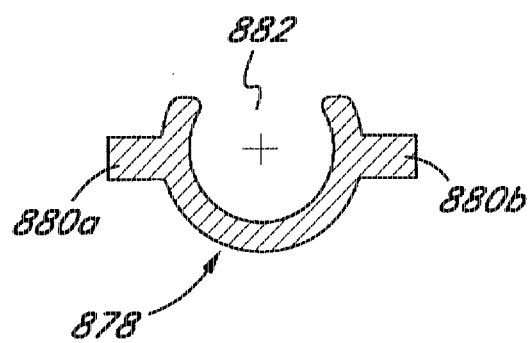
Figure 14:
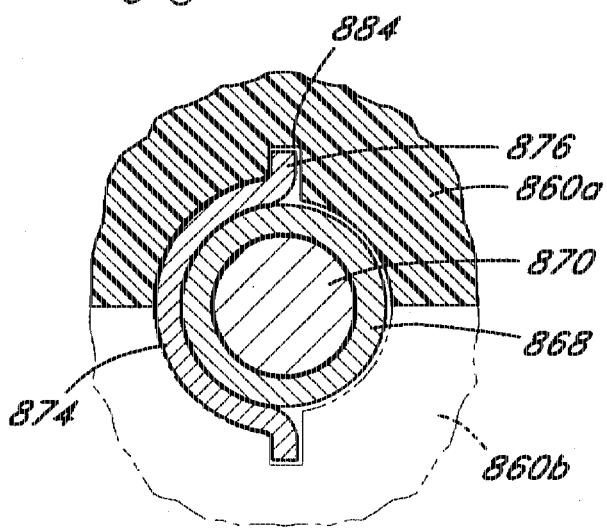
FIG. 14 is a cross sectional view of the needle carrier and guide track taken upon the lines of 14—14 on FIG. 12.

The needle carrier 868 may also be formed by another method. FIG. 13B shows a cross sectional view of a needle carrier 878 which has been formed out of, for example, a 17-4 stainless steel alloy by a process called metal injection molding. This process allows the needle carrier 878 to be formed in a monolithic fashion such that bearing wings 880a,b and saddle 882 may be formed in one piece, along with other features of the needle carrier previously described. Other processes, such as die casting, investment casting, or powdered metal could also be used to create a monolithic needle carrier 878.

Figure 11A:
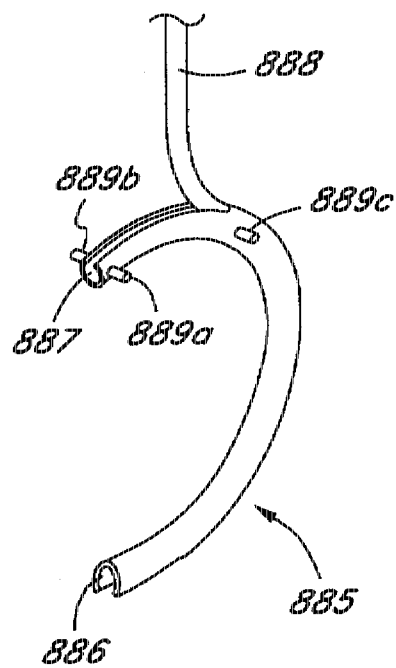
FIG. 11A is a detailed perspective view illustrating the general structure of an alternate embodiment of the needle carrier.

Another embodiment of the needle carrier is shown in FIG. 11A, where there is shown a needle carrier 885 which includes a socket 886 at the distal end adapted to hold a shouldered needle and a groove 887 at the proximal end adapted to contain a flexible needle driver 888 as previously described. Pins 889a,b,c,d are attached to the sides of the needle carrier 885. The pins 889 are dimensioned to be slidably disposed within, referring to FIG. 11, the groove 884 in the needle carrier guide track 864, and to provide guidance and stability to the needle carrier 885 in a fashion similar to that to be described with reference to FIG. 11 below.

Figure 15:
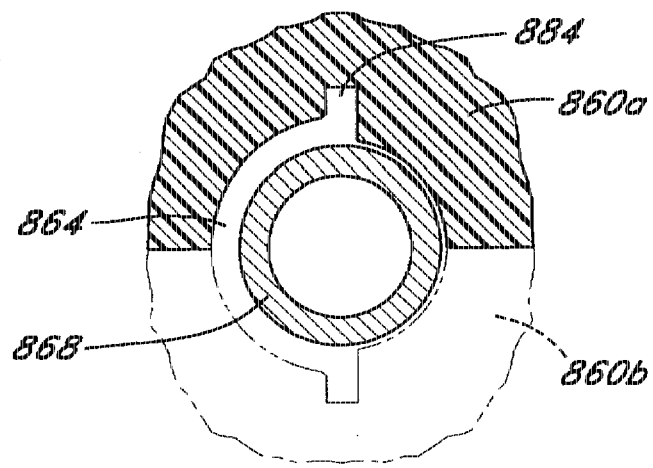
FIG. 15 is a cross sectional view of the needle carrier and guide track taken upon the lines of 15—15 on FIG. 12.

Referring again to FIG. 11, the needle carrier 868 and flexible carrier driver 870 are joined as previously described at saddle 872 of the needle carrier 868, which incorporates bearing wings 876a,b. The distal end 882 of the needle carrier 868 is adapted to accept a shouldered bullet needle of the type previously described in other embodiments. In this embodiment, the needle carrier guide track 864 further incorporates a groove 884 adapted to receive the bearing wings 876a,b. By referring to FIG. 14, a detailed cross sectional view of the groove 884 and the bearing wings 876, taken along the lines of the section arrows 14----14 shown in FIG. 12, may clearly be seen. FIG. 15 is a detailed cross sectional view of the needle carrier guide track 864 taken along the lines of the section arrows 15----15 shown in FIG. 12, and illustrates an area of the needle carrier 868 and of the needle carrier guide track 864 where there are no bearing wings 876a,b. It should be understood that the cross section shown in FIG. 15 of the needle carrier 868 could be of solid material instead of tubular material if the cross section were illustrating a monolithic part such as the needle carrier 878. It may also be understood from the foregoing illustrations, that the width and depth of the bearing wings 876a,b shown in FIG. 13A and the bearing wings 880a,b shown in FIG. 13B are not to be taken as literal illustrations of the physical dimensions of those features, as the width and depth may be varied in order to achieve more or less guidance and bearing surface area as the designer deems appropriate.

The operation of the embodiment described in FIGS. 11 through 15 is identical to that previously described in FIGS. 8C and 8D, with the exception that the bearing wings 876a,b are adapted to rotationally slide in the grooves 884a,b of the housing halves 860a,b. This provides axial and torsional guidance and resistance to deflection of the needle carrier 868 from the anticipated path. Performance improvements over the embodiment described in FIGS. 8C and 8D relate primarily to an increased ability to be able to torque and/or lift the device while the needle carrier is exposed to the tissues to be sutured.

The preferred material for the flexible carrier driver 870 is an alloy of nickel and titanium known in the art as nitinol. This material has both austenitic and martensitic forms, and can be alloyed to exhibit properties of both forms as the material moves through a transition temperature that can be varied. The martensitic form of the alloy, when processed into, for example, wire, has a lead-solder like consistency, and easily deflects plastically to a certain point, beyond which a considerable amount of force is necessary to cause further deflection. This elastic behavior in this regime is what allows the material to be both flexible and exhibit high column strength when properly constrained. As long as the wire is not required to bend around a radius which deflects the material past the plastic limit, the wire does not offer significant spring force. However, if it is required that the wire be bent around a tight radius, and the wire enters the elastic part of the stress/strain curve, substantial spring force may be exhibited. In the case of the above described embodiments, this spring force can create considerable drag in the drive system, reducing the tactile sense of feedback available to the surgeon. Thus it may be seen that a reduction in the amount of drag in the drive system may improve the tactile feedback to the user.

Accordingly, additional embodiments of the flexible carrier driver guide track are illustrated in FIGS. 16 and 17. Referring first to FIG. 16, there may be seen a detailed plan view of the distal end of an elongate cannular body 890 which is comprised of housing halves 892a,b. It is to be understood that for clarity only one of the housing halves 892 of the cannular body 890 is shown in FIG. 16. Housing half 892 includes a guided pathway 894 which includes a flexible carrier driver guide track 896 which intercepts a needle carrier guide track 898. At this intersection of the flexible carrier driver guide track 896 and the needle carrier guide track 898, lines which are tangent to the flexible carrier driver guide track 896 and the needle carrier guide track 898 are substantially parallel. Although it is not illustrated again here, by referring to FIGS. 14 and 15, it may be understood that the assembly of housing halves 892 together creates a closed tunnel-like pathway from the semi-circular cross sections of the guided pathways 894 and the needle carrier guide tracks 898. A flexible carrier driver 900 is slidably disposed within the guided pathway 894, and is suitably attached to a needle carrier 902 which is slidably and rotably disposed within the needle carrier guide track 898. It may be seen that the bend radius of the flexible carrier driver 900 in FIG. 16 is significantly larger than the bend radius of, for example in FIG. 12, the flexible carrier driver 870. This increased bend radius significantly reduces the spring forces exerted on the walls of the guided pathway 894 by the flexible carrier driver 900.

Another method of dealing with the friction created by the spring forces is to convert the sliding friction into rolling friction by means of interposing a bearing in the guide path. Therefor, we now describe by referring to FIG. 17 an embodiment which includes an elongate cannular body 910 (distal end shown) which is comprised of housing halves 912a,b. It is to be understood that for clarity only one of the housing halves 912 of the cannular body 910 is shown in FIG. 17. Housing half 912 includes a guided pathway 914 which includes a flexible carrier driver guide track 916 which intercepts a needle carrier guide track 918. A flexible carrier driver 920 is slidably disposed within the flexible carrier driver guide track 916, and is bent around a bearing 922, which is rotatably affixed to a pivot 924 such that the bearing 922 may spin freely about it's axis. When the flexible carrier driver 920 slides in the guided pathway 914 and is forced around the bearing 922, the spring forces created by the bending of the flexible carrier driver 920 are translated into rotational movement of the bearing 922 about the pivot 924, thus reducing the amount of frictional drag in the overall drive system.

As it may be obvious to those skilled in the art, another way of dealing with the frictional drag in the drive system is to reduce the coefficients of friction of the components. One such way of accomplishing this task is to fabricate the housing halves out of a lubricious material. As injection molding is a preferred method of fabrication of the housing halves, a molding material which has the appropriate physical properties to withstand the torsional and shear loadings imposed during use of the device, as well as having low surface friction would be desirable. An example of this kind of material is a molybdenum disulfide filled nylon.

It may also be apparent that the aforementioned process of metal injection molding may be used to fabricate the housing halves. If this process is used, however, the high surface friction generated by the metal needle carrier and the metal guide track must be overcome by modifying either the needle carrier or the housing halves with a surface treatment which lowers the surface friction. There are numerous surface treatments available for treating stainless steel parts to reduce their coefficients of friction. Among them are dry film lubricants, titanium nitride, and nickel alloys infused with various polymers such as PTFE or PVDF.

It will be understood that the apparatus and method of the present invention for an endoscopic suture system may be employed in numerous specific embodiments in addition to those described herein. Thus, these numerous other embodiments of the invention, which will be obvious to one skilled in the art, including but not limited to changes in the dimensions of the device, the type of materials employed, the location and type of needles, driving mechanisms, catching mechanisms, needle loading mechanisms, etc., are to be included within the scope of the present invention. The apparatus and method of the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A suturing instrument comprising:
   an elongate body member having a longitudinal axis;
   a needle deployment system located within a distal end portion of said elongate body member, said needle deployment system comprising:
   a curved needle carrier channel having a guide groove formed therein;
   a curved needle carrier movably positioned in said curved needle carrier channel, said curved needle carrier having a guide wing which engages said guide groove formed in said curved needle carrier channel thereby guiding and stabilizing said curved needle carrier within said curved needle carrier channel; and
   a deployment controller having a proximal end, a distal end, a retracted position and a deployed position, said deployment controller extending substantially along the longitudinal axis of said elongate body member to the distal end of said elongate body member where it is coupled to said curved needle carrier and moves said curved needle carrier through said curved needle carrier channel as it moves between said retracted position and said deployed position.

2. A suturing instrument as defined in claim 1 wherein said deployment controller further comprises an internal driver pathway extending from a proximate end portion of said elongate body member to said distal end portion of said elongate body member, wherein said internal driver pathway composes a curved pathway section near said distal end portion of said elongate body member, said curved pathway section having a distal end curvature.

3. A suturing instrument as defined in claim 2 further comprising a channel intersection at a location where a protection of a centerline of said distal end curvature of said curved pathway section from said distal end of said curved pathway section into said curved needle carrier channel is substantially tangent to a centerline of said curved needle carrier channel.

4. A suturing instrument as defined in claim 3 wherein said deployment controller further comprises a flexible driver member coupled to said curved needle carrier, said flexible driver member being slidably disposed in said curved pathway section of said internal driver pathway.

5. A suturing instrument as defined in claim 4 wherein said flexible driver member further comprises an alloy of nickel and titanium.

6. A suturing instrument as defined in claim 1 wherein said curved needle carrier guide wing further comprises a plurality of pins.

7. A suturing instrument as defined in claim 4 further comprising a rolling bearing member positioned adjacent said curved pathway section of said internal driver pathway and said channel intersection such that said flexible driver member contacts said rolling bearing member.

8. A suturing instrument comprising:
   an elongate body member having a longitudinal axis;
   a curved needle carrier channel positioned in said elongate body member wherein said curved needle carrier channel has a guide groove formed therein; and
   a curved needle carrier movably positioned in said curved needle carrier channel, said curved needle carrier having a guide wing which engages said guide groove formed in said curved needle carrier channel thereby guiding and stabilizing said curved needle carrier within said curved needle carrier channel.

9. A suturing instrument as defined in claim 8 further comprising an internal driver pathway extending from a proximate end portion of said elongate body member to a distal end portion of said elongate body member, wherein said internal driver pathway comprises a curved pathway section near said distal end portion of said elongate body member, said curved pathway section having a distal end curvature.

10. A suturing instrument as defined in claim 9 further comprising a channel intersection at a location where a projection of a centerline of said distal end curvature of said curved pathway section from said distal end of said curved pathway section into said curved needle carrier channel is substantially tangent to a centerline of said curved needle carrier channel.

11. A suturing instrument as defined in claim 10 further comprising a flexible driver member coupled to said curved needle carrier, said flexible driver member being slidably disposed in said curved pathway section of said internal driver pathway.

12. A suturing instrument as defined in claim 11 wherein said flexible driver member further comprises an alloy of nickel and titanium.

13. A suturing instrument as defined in claim 8 wherein said curved needle carrier guide wing further comprises a plurality of pins.

14. A suturing instrument as defined in claim 11 further comprising a rolling bearing member positioned adjacent said internal driver pathway and said channel intersection such that said flexible driver member contacts said rolling bearing member.

15. A method of stabilizing and guiding a curved needle carrier movably positioned in a curved needle carrier channel, said method comprising:
    providing a first guide groove and a second guide groove in the curved needle carrier channel;
    providing a first guide wing and a second guide wing on the curved needle carrier; and
    positioning the curved needle carrier within the curved needle carrier channel such that the first guide wing on the curved needle carrier slidably engages the first guide groove in the curved needle carrier channel and the second guide wing on the curved needle carrier slidably engages the second guide groove in the curved needle carrier channel.

16. A suturing instrument comprising:
    an elongate body member;
    a curved tubular channel positioned in a distal end portion of said body member, wherein said curved tubular channel further comprises:
        a length defined by a proximate end and a distal end; and
        a bearing groove formed along at least a portion of said curved tubular channel length; and
    a curved needle carrier movably positioned in said curved tubular channel, said curved needle carrier having a bearing wing which engages said bearing groove formed in said curved tubular channel thereby guiding and stabilizing said curved needle carrier movably positioned within said curved tubular channel.

17. A suturing instrument as defined in claim 16 further comprising an internal driver pathway extending from a proximate end portion of said elongate body member to a distal end portion of said elongate body member, wherein said internal driver pathway comprises a curved pathway section near said distal end portion of said elongate body member, said curved pathway section having a distal end curvature.

18. A suturing instrument as defined in claim 17 further comprising a channel intersection at a location where a projection of a centerline of said distal end curvature of said curved pathway section from said distal end of said curved pathway section into said curved tubular channel is substantially tangent to a centerline of said curved tubular channel.

19. A suturing instrument as defined in claim 18 further comprising a flexible driver member coupled to said curved needle carrier, said flexible driver member being slidably disposed in said curved pathway section of said internal driver pathway.

20. A suturing instrument as defined in claim 19 wherein said flexible driver member further comprises an alloy of nickel and titanium.

21. A suturing instrument as defined in claim 19 further comprising a rolling bearing member positioned adjacent said internal driver pathway and said channel intersection such that said flexible driver member contacts said rolling bearing member.

22. A suturing instrument as defined in claim 16 wherein said curved needle carrier bearing wing further comprises a plurality of pins.

23. A suturing instrument comprising:
    an elongate body member having a longitudinal axis;
    an internal driver pathway extending from a proximate end portion to a distal end portion of said elongate body member, wherein said internal driver pathway comprises a curved pathway section near said distal end portion of said elongate body member, said curved pathway section having a distal end curvature;
    a curved needle carrier channel located near the distal end portion of said elongate body member; and
    a channel intersection at a location where a projection of a centerline of said distal end curvature of said curved pathway section from said distal end of said curved pathway section into said curved needle carrier channel is substantially tangent to a centerline of said curved needle carrier channel.

24. A suturing instrument as defined in claim 23 further comprising a curved needle carrier movably positioned in said curved needle carrier channel.

25. A suturing instrument as defined in claim 24 further comprising a flexible driver member coupled to said curved needle carrier, said flexible driver member being slidably disposed in said curved pathway section of said internal driver pathway.

26. A suturing instrument as defined in claim 25 wherein said flexible driver member further comprises an alloy of nickel and titanium.

27. A suturing instrument as defined in claim 25 further comprising a rolling bearing member positioned adjacent said curved pathway section of said internal driver pathway and said channel intersection such that said flexible driver member contacts said rolling bearing member.

28. A suturing instrument comprising:
    an elongate body member having a longitudinal axis;
    a curved needle carrier channel having a guide track formed therein, said curved needle carrier channel located within said elongate body member at a distal end thereof, said curved needle carrier channel located substantially in a plane which is substantially parallel to said elongate body member longitudinal axis, said curved needle carrier channel forming a needle exit port in a side wall of said elongate body member; and
    a curved needle carrier movably positioned in said curved needle carrier channel, said curved needle carrier having a guide wing which engages said guide track formed in said curved needle carrier channel thereby guiding and stabilizing said curved needle carrier within said curved needle carrier channel.

29. A suturing instrument as defined in claim 28 further comprising an internal driver pathway extending from a proximate end portion of said elongate body member to a distal end portion of said elongate body member, where said internal driver pathway comprises a curved pathway section near said distal end portion of said elongate body member, said curved pathway section having a distal end curvature.

30. A suturing instrument as defined in claim 29 further comprising a channel intersection at a location where a projection of a centerline of said distal end curvature of said curved pathway section from said distal end of said curved pathway section into said curved needle carrier channel is substantially tangent to a centerline of said curved needle carrier channel.

31. A suturing instrument as defined in claim 30 further comprising a flexible driver member coupled to said curved needle carrier, said flexible driver member being slidably disposed in said curved pathway section of said internal driver pathway.

32. A suturing instrument as defined in claim 31 wherein said flexible driver member further comprises an alloy of nickel and titanium.

33. A suturing instrument as defined in claim 31 further comprising a rolling bearing member positioned adjacent said internal driver pathway and said channel intersection such that said flexible driver member contacts said rolling bearing member.

34. A suturing instrument as defined in claim 28 wherein said curved needle carrier guide wing further comprises a plurality of pins.

35. A suturing instrument comprising:

an elongate body member;

a curved tubular channel positioned in a distal end portion of said body member, wherein said curved tubular channel further comprises:
  a length defined by a proximate end and a distal end; and
  a bearing groove formed along at least a portion of said curved tubular channel length; and a curved suture carrier movably positioned in said curved tubular channel, said curved suture carrier having a bearing wing which engages said bearing groove formed in said curved tubular channel thereby guiding and stabilizing said curved suture carrier movably positioned within said curved tubular channel.

36. A suturing instrument as defined in claim 35 further comprising an internal driver pathway extending from a proximate end portion of said elongate body member to a distal end portion of said elongate body member, wherein said internal driver pathway comprises a curved pathway section near said distal end portion of said elongate body member, said curved pathway section having a distal end curvature.

37. A suturing instrument as defined in claim 36 further comprising a channel intersection at a location where a projection of a centerline of said distal end curvature of said curved pathway section from said distal end of said curved pathway section into said curved tubular channel is substantially tangent to a centerline of said curved tubular channel.

38. A suturing instrument as defined in claim 37 further comprising a flexible driver member coupled to said curved suture carrier, said flexible driver member being slidably disposed in said curved pathway section of said internal driver pathway.

39. A suturing instrument as defined in claim 38 wherein said flexible driver member further comprises an alloy of nickel and titanium.

40. A suturing instrument as defined in claim 38 further comprising a rolling bearing member positioned adjacent said internal driver pathway and said channel intersection such that said flexible driver member contacts said rolling bearing member.

41. A suturing instrument as defined in claim 35 wherein said curved suture carrier bearing wing further comprises a plurality of pins.

42. A suturing instrument comprising:

an elongate body member having a longitudinal axis;

a curved suture carrier channel having a guide track formed therein, said curved suture carrier channel located within said elongate body member at a distal end thereof, said curved suture carrier channel located substantially in a plane which is substantially parallel to said elongate body member longitudinal axis, said curved suture carrier channel forming an exit port in a side wall of said elongate body member; and a curved suture carrier movably positioned in said curved suture carrier channel, said curved suture carrier having a guide wing which engages said guide track formed in said curved suture carrier channel thereby guiding and stabilizing said curved suture carrier within said curved suture carrier channel.

43. A suturing instrument as defined in claim 42 further comprising an internal driver pathway extending from a proximate end portion of said elongate body member to a distal end portion of said elongate body member, wherein said internal driver pathway comprises a curved pathway section near said distal end portion of said elongate body member, said curved pathway section having a distal end curvature.

44. A suturing instrument as defined in claim 43 further comprising a channel intersection at a location where a projection of a centerline of said distal end curvature of said curved pathway section from said distal end of said curved pathway section into said curved suture carrier channel is substantially tangent to a centerline of said curved suture carrier channel.

45. A suturing instrument as defined in claim 44 further comprising a flexible driver member coupled to said curved suture carrier, said flexible driver member being slidably disposed in said curved pathway section of said internal driver pathway.

46. A suturing instrument as defined in claim 45 wherein said flexible driver member further comprises an alloy of nickel and titanium.

47. A suturing instrument as defined in claim 45 further comprising a rolling bearing member positioned adjacent said internal driver pathway and said channel intersection such that said flexible driver member contacts said rolling bearing member.

48. A suturing instrument as defined in claim 42 wherein said curved suture carrier guide wing further comprises a plurality of pins.

* * * * *